US012359263B2

(12) United States Patent
Cantet et al.

(10) Patent No.: US 12,359,263 B2
(45) Date of Patent: Jul. 15, 2025

(54) CUCUMBER PLANTS WITH IMPROVED PEST RESISTANCE

(71) Applicant: Seminis Vegetable Seeds, Inc., St. Louis, MO (US)

(72) Inventors: Melissa C. Cantet, Rotterdam (NL); Eva King-Fan Chan, Rosebery (AU); Maarten J. K. De Milliano, Enkhuizen (NL); Jeroen S. de Vries, Bergschenhoek (NL); Fengxing Du, Chesterfield, MO (US); Uri Krieger, Bergschenhoek (NL); Robyn L. Morgan, Riverside, CA (US); Antoon Stekelenburg, Houten (NL); Emilia M. Tomas, Almeria (ES); Wenwen Xiang, Davis, CA (US)

(73) Assignee: Seminis Vegetable Seeds, Inc., St. Louis, MO (US)

( * ) Notice: Subject to any disclaimer, the term of this patent is extended or adjusted under 35 U.S.C. 154(b) by 708 days.

(21) Appl. No.: 16/635,991

(22) PCT Filed: Aug. 1, 2018

(86) PCT No.: PCT/US2018/044780

§ 371 (c)(1),
(2) Date: Jan. 31, 2020

(87) PCT Pub. No.: WO2019/028126

PCT Pub. Date: Feb. 7, 2019

(65) Prior Publication Data

US 2021/0147950 A1 May 20, 2021

Related U.S. Application Data

(60) Provisional application No. 62/541,042, filed on Aug. 3, 2017.

(51) Int. Cl.

| | |
|---|---|
| ***A01H 5/08*** | (2018.01) |
| ***A01H 1/00*** | (2006.01) |
| ***A01H 1/04*** | (2006.01) |
| ***A01H 6/34*** | (2018.01) |
| ***C12Q 1/6895*** | (2018.01) |

(52) U.S. Cl.
CPC ............. *C12Q 1/6895* (2013.01); *A01H 1/00* (2013.01); *A01H 1/045* (2021.01); *A01H 1/1255* (2021.01); *A01H 5/08* (2013.01); *A01H 6/346* (2018.05)

(58) Field of Classification Search
None
See application file for complete search history.

(56) References Cited

U.S. PATENT DOCUMENTS

| | | | | |
|---|---|---|---|---|
| 8,841,516 | B2 | 9/2014 | De Milliano et al. | |
| 8,895,812 | B2 | 11/2014 | Hofstede et al. | |
| 2008/0307540 | A1 | 12/2008 | Hofstede et al. | |
| 2012/0066790 | A1 * | 3/2012 | de Milliano et al. | A01H 5/00 |

FOREIGN PATENT DOCUMENTS

| | | |
|---|---|---|
| WO | WO 2002/062130 | 8/2002 |
| WO | WO 2010/098670 | 9/2010 |
| WO | WO 2017/016908 | 2/2017 |

OTHER PUBLICATIONS

"Cucumber (Chinese Long) v2 Genome," CuGenDB, http://cucurbitgenomics.org/organism/2, Accessed on Mar. 16, 2020.
International Search Report for PCT/US18/044780, dated Oct. 22, 2018.
International Written Opinion for PCT/US18/044780, dated Oct. 22, 2018.
TSA: *Cucumis sativus* var. *sativus cultivar* Vlaspik CuSa20091020433, mRNA sequence; GenBank JW938393.1; 2012.

* cited by examiner

*Primary Examiner* — Phuong T Bui
(74) *Attorney, Agent, or Firm* — Dentons US LLP

(57) ABSTRACT

Cucumber plants exhibiting resistance to *Fusarium oxysporum f.sp. radicis cucumerinum* (FORC) are provided, together with methods of producing, identifying, or selecting plants or germplasm with a FORC resistance phenotype. Such plants include cucumber plants comprising introgressed genomic regions conferring disease resistance. Compositions, including novel polymorphic markers for detecting plants comprising introgressed disease resistance alleles, are further provided.

7 Claims, 1 Drawing Sheet

Specification includes a Sequence Listing.

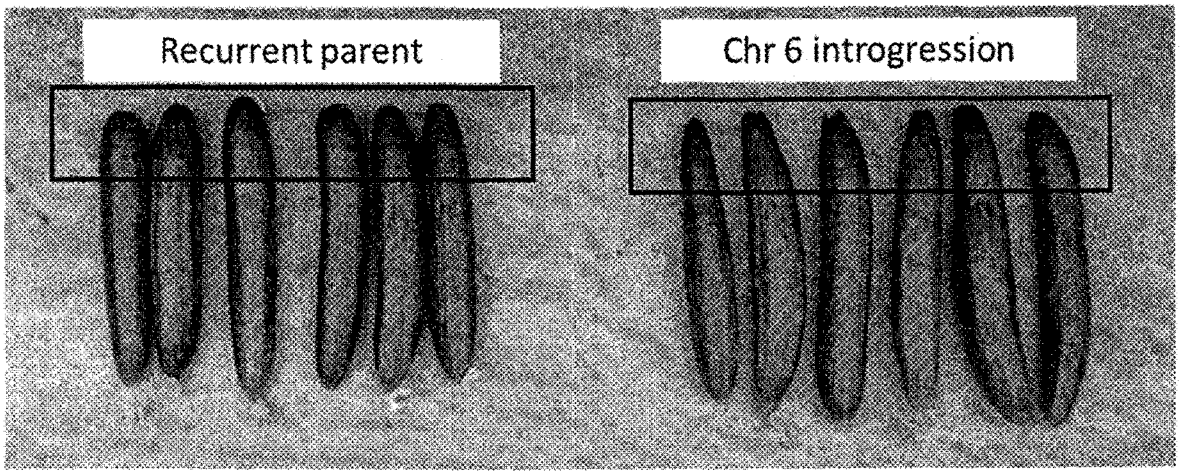
Recurrent parent
Chr 6 introgression

CUCUMBER PLANTS WITH IMPROVED PEST RESISTANCE

REFERENCE TO RELATED APPLICATION

This application is a 371 National Stage application of International Application No. PCT/US18/44780, filed Aug. 1, 2018, which claims the benefit of U.S. Provisional Application No. 62/541,042, filed on Aug. 3, 2017, which are incorporated herein by reference in their entireties.

INCORPORATION OF SEQUENCE LISTING

A sequence listing containing the file named "SEMB027WO_ST25.txt" which is 24.7 kilobytes (measured in MS-Windows®) and created on Jul. 31, 2018, and comprises 55 sequences, is incorporated herein by reference in its entirety.

FIELD OF THE INVENTION

The present invention relates to the field of plant breeding and more specifically to methods and compositions for producing cucumber plants exhibiting improved pest resistance.

BACKGROUND

Disease resistance is an important trait in agriculture, particularly for the production of food crops. Although disease resistance alleles have been identified in cucumber, efforts to introduce these alleles into cultivated lines have been hindered by a lack of specific markers linked to the alleles, as well as linkage drag that leads to unacceptable fruit quality. The use of marker-assisted selection (MAS) in plant breeding has made it possible to select plants based on genetic markers linked to traits of interest. However, accurate markers for identifying or tracking desirable traits in plants are frequently unavailable even if a gene associated with the trait has been characterized. These difficulties are further complicated by factors such as polygenic or quantitative inheritance, epistasis, and an often incomplete understanding of the genetic background underlying expression of a desired phenotype. In the absence of accurate and validated markers for use in MAS, it may not be feasible to produce new plant lines exhibiting certain disease resistance phenotypes and acceptable fruit quality.

SUMMARY

In one aspect, the invention provides a *Cucumis sativus* plant comprising an introgressed *Fusarium oxysporum f.sp. radicis cucumerinum* (FORC) resistance allele within a recombinant chromosomal segment flanked in the genome of said plant by: a) marker locus SNP_Marker6 (SEQ ID NO:26) and marker locus SNP_Marker7 (SEQ ID NO: 31) on chromosome 6; or b) marker locus SNP_Marker1 (SEQ ID NO:1) and marker locus SNP_Marker2 (SEQ ID NO:6) on chromosome 3; wherein said introgressed FORC resistance allele confers to said plant increased resistance to FORC compared to a plant not comprising said allele, and wherein said plant lacks a deleterious allele genetically linked to said FORC resistance allele that confers increased necrosis or decreased fruit quality to said plant when present. In some embodiments, said introgressed FORC resistance allele is within a recombinant chromosomal segment flanked in the genome of said plant marker locus SNP_Marker6 (SEQ ID NO:26) and marker locus SNP_Marker7 (SEQ ID NO: 31), and wherein said plant further comprises a further FORC resistance allele within a chromosomal segment flanked in the genome of said plant by marker locus SNP_Marker1 (SEQ ID NO: 1) and marker locus SNP_Marker2 (SEQ ID NO:6) on chromosome 3. In further embodiments, said recombinant chromosomal segment is flanked in the genome of said plant by marker locus SNP_Marker6 (SEQ ID NO:26) and marker locus SNP_Marker11 (SEQ ID NO:51) on chromosome 6. In yet further embodiments, said recombinant chromosomal segment is flanked in the genome of said plant by marker locus SNP_Marker4 (SEQ ID NO:16) and marker locus SNP_Marker5 (SEQ ID NO:21) on chromosome 6. In other embodiments, said recombinant chromosomal segment comprises a marker locus selected from the group consisting of SNP_Marker6 (SEQ ID NO:26), marker locus SNP_Marker8 (SEQ ID NO:36), marker locus SNP_Marker4 (SEQ ID NO:16), marker locus SNP_Marker9 (SEQ ID NO:41), marker locus SNP_Marker10 (SEQ ID NO:46), marker locus SNP_Marker5 (SEQ ID NO:21), and SNP_Marker11 (SEQ ID NO:51) on chromosome 6.

In certain embodiments, said recombinant chromosomal segment comprises: a) a non-introgressed allele at marker locus SNP_Marker6 (SEQ ID NO:26), a non-introgressed allele at marker locus SNP_Marker8 (SEQ ID NO:36), an introgressed allele at marker locus SNP_Marker4 (SEQ ID NO:16), an introgressed allele at marker locus SNP_Marker5 (SEQ ID NO:21), an introgressed allele at marker locus SNP_Marker9 (SEQ ID NO:41), an introgressed allele at marker locus SNP_Marker10 (SEQ ID NO:46) on chromosome 6; b) a non-introgressed allele at marker locus SNP_Marker11 (SEQ ID NO:51), an introgressed allele at marker locus SNP_Marker4 (SEQ ID NO:16), an introgressed allele at marker locus SNP_Marker5 (SEQ ID NO:21), an introgressed allele at marker locus SNP_Marker9 (SEQ ID NO:41), an introgressed allele at marker locus SNP_Marker110 (SEQ ID NO:46) on chromosome 6; or c) a non-introgressed allele at marker locus SNP_Marker6 (SEQ ID NO:26), a non-introgressed allele at marker locus SNP_Marker8 (SEQ ID NO:36), a non-introgressed allele at marker locus SNP_Marker11 (SEQ ID NO:51), an introgressed allele at marker locus SNP_Marker4 (SEQ ID NO:16), an introgressed allele at marker locus SNP_Marker5 (SEQ ID NO:21), an introgressed allele at marker locus SNP_Marker9 (SEQ ID NO:41), an introgressed allele at marker locus SNP_Marker10 (SEQ ID NO:46) on chromosome 6.

In further embodiments, said recombinant chromosomal segment is flanked in the genome of said plant by marker locus SNP_Marker1 (SEQ ID NO:1) and SNP_Marker2 (SEQ ID NO:6) on chromosome 3. In additional embodiments, said recombinant chromosomal segment comprises a marker locus selected from the group consisting of SNP_Marker1 (SEQ ID NO:1), marker locus SNP_Marker3 (SEQ ID NO:11), and SNP_Marker2 (SEQ ID NO:6) on chromosome 3. The invention further provides plant parts of the plants provided herein.

In another aspect, the invention provides a recombinant DNA segment comprising a FORC resistance allele that confers to a plant increased resistance to FORC, and lacking a deleterious allele genetically linked to said FORC resistance allele that confers to a plant increased necrosis or decreased fruit quality. In certain embodiments, said first allele is derived from a plant of line URS189. In other embodiments, said recombinant DNA segment comprises a sequence selected from the group consisting of SEQ ID NOs: 1, 6, 11, 16, 21, 26, 31, 36, 41, 46, and 51. In further embodiments, said recombinant DNA segments is further defined as comprised within a plant, plant part, plant cell, or seed. In yet further embodiments, said DNA segment confers increased resistance to FORC to said plant.

In yet another aspect, the invention provides methods for producing a *Cucumis sativus* plant exhibiting resistance to FORC, comprising: a) crossing the *Cucumis sativus* plant provided herein with itself or with a second *Cucumis sativus* plant of a different genotype to produce one or more progeny plants; and b) selecting a progeny plant comprising said FORC resistance allele. In some embodiments, selecting said progeny plant comprises identifying a genetic marker genetically linked to said FORC resistance allele. In further embodiments, selecting said progeny plant comprises identifying a genetic marker within or genetically linked to a chromosomal segment flanked in the genome of said plant by: a) marker locus SNP_Marker6 (SEQ ID NO:26) and marker locus SNP_Marker7 (SEQ ID NO:31) on chromosome 6; b) marker locus SNP_Marker6 (SEQ ID NO:26) and marker locus SNP_Marker11 (SEQ ID NO:51) on chromosome 6; or c) marker locus SNP_Marker1 (SEQ ID NO:1) and SNP_Marker2 (SEQ ID NO:6) on chromosome 3. In yet further embodiments, selecting a progeny plant comprises detecting at least one polymorphism at a locus selected from the group consisting of marker locus SNP_Marker1 (SEQ ID NO:1), marker locus SNP_Marker2 (SEQ ID NO:6), marker locus SNP_Marker3 (SEQ ID NO:11), marker locus SNP_Marker4 (SEQ ID NO:16), marker locus SNP_Marker5 (SEQ ID NO:21), marker locus SNP_Marker6 (SEQ ID NO:26), marker locus SNP_Marker7 (SEQ ID NO:31), marker locus SNP_Marker8 (SEQ ID NO:36), marker locus SNP_Marker9 (SEQ ID NO:41), marker locus SNP_Marker10 (SEQ ID NO:46), and marker locus SNP_Marker11 (SEQ ID NO:51). In other embodiments, said FORC resistance allele is identified by detecting: a) a recurrent parent allele at marker locus SNP_Marker6 (SEQ ID NO:26), a recurrent parent allele at marker locus SNP_Marker8 (SEQ ID NO:36), a donor allele at marker locus SNP_Marker4 (SEQ ID NO:16), a donor allele at marker locus SNP_Marker5 (SEQ ID NO:21), a donor allele at marker locus SNP_Marker9 (SEQ ID NO:41), a donor allele at marker locus SNP_Marker10 (SEQ ID NO:46) on chromosome 6; b) a recurrent parent allele at marker locus SNP_Marker11 (SEQ ID NO:51), a donor allele at marker locus SNP_Marker4 (SEQ ID NO:16), a donor allele at marker locus SNP_Marker5 (SEQ ID NO:21), a donor allele at marker locus SNP_Marker9 (SEQ ID NO:41), a donor allele at marker locus SNP_Marker10 (SEQ ID NO:46) on chromosome 6; or c) a recurrent parent allele at marker locus SNP_Marker6 (SEQ ID NO:26), a recurrent parent allele at marker locus SNP_Marker8 (SEQ ID NO:36), a recurrent parent allele at marker locus SNP_Marker11 (SEQ ID NO:51), a donor allele at marker locus SNP_Marker4 (SEQ ID NO:16), a donor allele at marker locus SNP_Marker5 (SEQ ID NO:21), a donor allele at marker locus SNP_Marker9 (SEQ ID NO:41), a donor allele at marker locus SNP_Marker10 (SEQ ID NO:46) on chromosome 6. In certain embodiments, said progeny plant is an $F_2$-$F_6$ progeny plant. In further embodiments, producing said progeny plant comprises backcrossing.

In a further aspect, the invention provides methods of producing a *Cucumis sativus* plant exhibiting resistance to FORC, comprising introgressing into a plant a FORC resistance allele within a recombinant chromosomal segment flanked in the genome of said plant by: a) marker locus SNP_Marker6 (SEQ ID NO:26) and marker locus SNP_Marker7 (SEQ ID NO: 31) on chromosome 6; orb) marker locus SNP_Marker1 (SEQ ID NO: 1) and marker locus SNP_Marker2 (SEQ ID NO:6) on chromosome 3; wherein said introgressed FORC resistance allele confers to said plant increased resistance to FORC compared to a plant not comprising said allele, and wherein said recombinant chromosomal segment lacks a deleterious allele genetically linked to said FORC resistance allele that confers increased necrosis or decreased fruit quality to said plant when present. In certain embodiments, said introgressed FORC resistance allele is within a recombinant chromosomal segment flanked in the genome of said plant marker locus SNP_Marker6 (SEQ ID NO:26) and marker locus SNP_Marker7 (SEQ ID NO: 31), and wherein said plant further comprises a further FORC resistance allele within a chromosomal segment flanked in the genome of said plant by marker locus SNP_Marker1 (SEQ ID NO: 1) and marker locus SNP_Marker2 (SEQ ID NO:6) on chromosome 3. In further embodiments, said recombinant chromosomal segment is flanked in the genome of said plant by marker locus SNP_Marker6 (SEQ ID NO:26) and marker locus SNP_Marker11 (SEQ ID NO:51) on chromosome 6. In yet further embodiments, said recombinant chromosomal segment is defined by: a) a recurrent parent allele at marker locus SNP_Marker6 (SEQ ID NO:26), a recurrent parent allele at marker locus SNP_Marker8 (SEQ ID NO:36), a donor allele at marker locus SNP_Marker4 (SEQ ID NO:16), a donor allele at marker locus SNP_Marker5 (SEQ ID NO:21), a donor allele at marker locus SNP_Marker9 (SEQ ID NO:41), a donor allele at marker locus SNP_Marker10 (SEQ ID NO:46); b) a recurrent parent allele at marker locus SNP_Marker6 (SEQ ID NO:26), a recurrent parent allele at marker locus SNP_Marker8 (SEQ ID NO:36), a recurrent parent allele at marker locus SNP_Marker11 (SEQ ID NO:51), a donor allele at marker locus SNP_Marker4 (SEQ ID NO:16), a donor allele at marker locus SNP_Marker5 (SEQ ID NO:21), a donor allele at marker locus SNP_Marker9 (SEQ ID NO:41), a donor allele at marker locus SNP_Marker10 (SEQ ID NO:46); or c) a recurrent parent allele at marker locus SNP_Marker11 (SEQ ID NO:51), a donor allele at marker locus SNP_Marker4 (SEQ ID NO:16), a donor allele at marker locus SNP_Marker5 (SEQ ID NO:21), a donor allele at marker locus SNP_Marker9 (SEQ ID NO:41), a donor allele at marker locus SNP_Marker10 (SEQ ID NO:46). In certain embodiments, introgressing comprises backcrossing, marker-assisted selection, or assaying for said FORC resistance. The invention further provides plants obtainable by the methods provided herein.

In yet a further aspect, the invention provides methods of selecting a *Cucumis sativus* plant exhibiting resistance to FORC, comprising: a) crossing the *Cucumis sativus* plant of claim 1 with itself or with a second *Cucumis sativus* plant of a different genotype to produce one or more progeny plants; and b) selecting a progeny plant comprising said FORC resistance allele. In some embodiments, selecting said progeny plant comprises identifying a genetic marker genetically linked to said FORC resistance allele. In further embodiments, selecting said progeny plant comprises identifying a genetic marker within or genetically linked to a chromosomal segment flanked in the genome of said plant flanked by: a) marker locus SNP_Marker6 (SEQ ID NO:26) and marker locus SNP_Marker7 (SEQ ID NO:31) on chromosome 6; b) marker locus SNP_Marker6 (SEQ ID NO:26)

and marker locus SNP_Marker11 (SEQ ID NO:51) on chromosome 6; or c) marker locus SNP_Marker1 (SEQ ID NO:1) and SNP_Marker2 (SEQ ID NO:6) on chromosome 3. In yet further embodiments, selecting a progeny plant comprises detecting at least one polymorphism at a locus selected from the group consisting of marker locus SNP_Marker1 (SEQ ID NO:1), marker locus SNP_Marker2 (SEQ ID NO:6), marker locus SNP_Marker3 (SEQ ID NO:11), marker locus SNP_Marker4 (SEQ ID NO:16), marker locus SNP_Marker5 (SEQ ID NO:21), marker locus SNP_Marker6 (SEQ ID NO:26), marker locus SNP_Marker7 (SEQ ID NO:31), marker locus SNP_Marker8 (SEQ ID NO:36), marker locus SNP_Marker9 (SEQ ID NO:41), marker locus SNP_Marker10 (SEQ ID NO:46), and marker locus SNP_Marker11 (SEQ ID NO:51). In some embodiments, said progeny plant is an $F_2$-$F_6$ progeny plant. In certain embodiments, producing said progeny plant comprises backcrossing.

BRIEF DESCRIPTION OF THE DRAWINGS

FIG. 1: Undesirable fruit shape characteristics in plants with the introgression of a newly identified QTL on chromosome 6. The fruit show elongated and thinner neck shape. A thin neck will result in a faster evaporation of water leading to a “rubbery” neck, which is perceived by consumers as spoiled fruit.

DETAILED DESCRIPTION

*Fusarium oxysporum f.sp. radicis cucumerinum* (FORC) is a soil-borne fungus that causes *Fusarium* stem and root rot in cucumber (*Cucumis sativus*) plants. FORC damages the vascular system of the cucumber plant and causes wilting or yellowing of leaves, stem, and roots, and eventual death of the plant. FORC is a common disease in protected culture environments where it often infects young plants, although in many cases symptoms do not appear until much later when fruit starts to set in adult plants. It is typically not feasible to control FORC during the growing season since chemical treatments may leave residue on harvestable fruit and are prohibited in many areas. In addition, supermarkets increasingly commit, under consumer pressure, to supply vegetable products with pesticide residue levels much lower than legally allowed, essentially prohibiting the use of these pesticides by growers of these vegetables.

Cucumber lines exhibiting resistance to FORC are known, and intensive efforts have been made to introgress FORC resistance alleles from these lines into other cultivated cucumber lines. However, these efforts have been of limited success because introgressed disease resistance alleles have, to date, been associated with undesirable agronomic traits, such as necrosis, poor fruit shape, and agronomically unacceptable plant architecture. Unacceptable fruit quality and yield loss due to FORC in cucumber plants therefore remains a significant problem.

Efforts to reduce the incidence or severity of undesirable traits in cucumber plants comprising FORC resistance introgressions have been further hindered by an incomplete understanding of the genetic factors controlling FORC resistance. In particular, markers and assays that accurately correlate genotype with disease resistance and fruit yield phenotypes over a variety of cucumbers types have previously been unavailable.

For the first time, the invention surprisingly has provided recombinant introgressions of FORC resistance alleles into cultivated cucumber lines without the deleterious traits that have previously been associated with FORC resistance. The novel recombinant introgressions provided by the invention result in plants which maintain plant vigor despite the presence of FORC, and which do not exhibit undesirable necrosis, poor fruit shape, or agronomically unacceptable plant architecture compared with plants not comprising the recombinant introgressions. The invention therefore represents a significant advance in the art. By further providing novel, accurate markers for tracking the introgressed alleles during plant breeding, the invention permits introgression of the disease resistance alleles into any desired cucumber genotype.

Despite the earlier obstacles to the successful use of FORC resistance alleles in elite cultivated cucumber lines, the present inventors were able to produce novel introgressions on chromosome 3 and chromosome 6 which confer resistance to FORC without the deleterious traits previously associated with disease resistance introgressions. In certain embodiments, plants are provided comprising an introgressed allele on chromosome 3 or 6, wherein said introgressed allele confers to said plant increased resistance to *Fusarium oxysporum f.sp. radicis cucumerinum* (FORC) compared to a plant not comprising said allele. In further embodiments, said plant lacks a further allele, genetically linked to said introgressed allele, that confers increased necrosis or decreased fruit quality when present. In yet further embodiments, plants are provided comprising introgressed alleles on both chromosomes 3 and 6, wherein said plant lacks an allele, genetically linked to said introgressed alleles, that confers increased necrosis or decreased fruit quality when present.

In some embodiments, such introgressions are defined as located within a 13 cM genomic interval between SNP_Marker6 (SEQ ID NO:26) and SNP_Marker7 (SEQ ID NO:31) on chromosome 6. SNP_Marker6 (SEQ ID NO:26) comprises a SNP change from C to T located at 4,904,085 bp of version 2 of the public cucumber genome of Chinese Cornell Long 9930. SNP_Marker7 (SEQ ID NO: 31) comprises a SNP change from A to G located at 8,038,585 bp of the public genome. In further embodiments, introgressions on chromosome 6 provided herein are defined as located within a 0.4 cM genomic interval between SNP_Marker4 (SEQ ID NO:16) and SNP_Marker5 (SEQ ID NO:21).

The invention further provides reduced recombinant introgressions comprising a genomic interval between SNP_Marker6 (SEQ ID NO:26) and SNP_Marker11 (SEQ ID NO:51), wherein said reduced genomic interval lacks linkage drag associated with larger FORC resistance introgressions. SNP_Marker11 (SEQ ID NO:51) comprises a SNP change from G to A located at 7,040,820 bp of the public cucumber genome of Chinese Cornell Long 9930. The invention further provides reduced recombinant introgressions comprising a genomic interval between SNP_Marker8 (SEQ ID NO:36) and SNP_Marker11 (SEQ ID NO:51), wherein said reduced genomic interval lacks linkage drag associated with larger FORC resistance introgressions. SNP_Marker8 (SEQ ID NO:36) comprises a SNP change from T to C at 4,904,085 by of version 2 of the public cucumber genome of Chinese Cornell Long 9930. In some embodiments, introgressions provided by the invention comprise a marker locus selected from the group consisting of marker locus SNP_Marker6 (SEQ ID NO:26), marker locus SNP_Marker8 (SEQ ID NO:36), marker locus SNP_Marker4 (SEQ ID NO:16), marker locus SNP_Marker9 (SEQ ID NO:41), marker locus SNP_Marker10 (SEQ ID NO:46), marker locus SNP_Marker5 (SEQ ID NO:21), and SNP_Marker11 (SEQ ID NO:51) on chromosome 6. Plants comprising the reduced recombinant introgressions of the invention and methods of producing such plants are further provided.

The invention further provides recombinant introgressions comprising a reduced genomic interval of approximately 0.4 cM between SNP_Marker4 (SEQ ID NO:16) and SNP_Marker5 (SEQ ID NO:21), wherein said reduced genomic interval lacks linkage drag associated with larger FORC resistance introgressions. SNP_Marker4 (SEQ ID NO:16) comprises a SNP change from G to C located at 5,809,537 bp of version 2 of the public cucumber genome of Chinese Cornell Long 9930. SNP_Marker5 (SEQ ID NO:21) comprises a SNP change from T to G located at 5,875,197 bp of the public genome. The invention further provides SNP_Marker9 (SEQ ID NO:41) as an interstitial marker between SNP_Marker4 (SEQ ID NO:16) and SNP_Marker5 (SEQ ID NO:21). SNP_Marker9 (SEQ ID NO:41) comprises a SNP change from C to T at 5,868,909 bp of version 2 of the public cucumber genome of Chinese Cornell Long 9930.

The invention further provides plants comprising a novel introgression on chromosome 3, defined as being located between SNP_Marker1 (SEQ ID NO:1) and SNP_Marker2 (SEQ ID NO:6), a 14.9 cM interval that can be selected with SNP_Marker3 (SEQ ID NO:11). SNP_Marker1 (SEQ ID NO:1) comprises a SNP change of A to G at 13,563,433 bp of the public genome. SNP_Marker2 (SEQ ID NO:6) comprises a SNP change of C to T at 22,338,746 bp of the public genome, and SNP_Marker3 (SEQ ID NO:11) comprises a SNP change of G to C at 17,602,782 of the public genome.

The invention further provides plants comprising reduced recombinant introgressions comprising a genomic region providing FORC resistance with a recombination event between SNP_Marker6 (SEQ ID NO:26) and SNP_Marker4 (SEQ ID NO:16) resulting in a reduced genomic interval lacking linkage drag associated traits associated with larger FORC resistance introgressions. The invention further provides reduced recombinant introgressions comprising a genomic region providing FORC resistance with a recombination event between SNP_Marker110 (SEQ ID NO:46) and SNP_Marker11 (SEQ ID NO:51) resulting in a reduced genomic interval lacking linkage drag associated traits associated with larger FORC resistance introgressions. SNP_Marker10 (SEQ ID NO:46) comprises a SNP change from A to T at 5,900,725 bp of version 2 of the public cucumber genome of Chinese Cornell Long 9930. The invention further provides reduced recombinant introgressions comprising a genomic region providing FORC resistance with a recombination event between SNP_Marker6 (SEQ ID NO:26) and SNP_Marker4 (SEQ ID NO:16) and a recombination event between SNP_Marker10 (SEQ ID NO:46) and SNP_Marker11 (SEQ ID NO:51) resulting in a reduced genomic interval lacking linkage drag associated traits associated with larger FORC resistance introgressions.

In other embodiments, the invention provides plants comprising on or more of the novel recombinant introgressions provided herein. These novel introgressions provide robust resistance to FORC, while avoiding the reduction in performance characteristics associated with conventional disease resistance alleles. The invention further provides novel trait-linked markers which can be used to produce plants comprising novel recombinant introgressions on chromosomes 3 and 6 conferring FORC resistance as described herein. In particular embodiments, the invention provides the markers shown in Table 3. Other embodiments of the invention provide markers SNP_Marker1 (SEQ ID NO:1), SNP_Marker2 (SEQ ID NO:6), SNP_Marker3 (SEQ ID NO:11), SNP_Marker4 (SEQ ID NO:16), SNP_Marker5 (SEQ ID NO:21), SNP_Marker6 (SEQ ID NO:26), SNP_Marker7 (SEQ ID NO:31), SNP_Marker8 (SEQ ID NO:36), SNP_Marker9 (SEQ ID NO:41), SNP_Marker10 (SEQ ID NO:46), and SNP_Marker11 (SEQ ID NO:51), which have been shown to be genetically linked to FORC resistance in plants.

The novel markers provided herein can be used to identify and track introgressions conferring resistance to FORC without the deleterious traits previously associated with FORC resistance alleles. In some embodiments, the present invention provides methods for producing plants comprising introgressed DNA within a genomic segment flanked by marker locus SNP_Marker6 (SEQ ID NO:26) and marker locus SNP_Marker7 (SEQ ID NO:31), or within a genomic segment flanked by marker locus SNP_Marker4 (SEQ ID NO:16) and marker locus SNP_Marker5 (SEQ ID NO:21), or within a genomic segment flanked by marker locus SNP_Marker6 (SEQ ID NO:26) and marker locus SNP_Marker11 (SEQ ID NO:51), or within a genomic segment flanked by marker locus SNP_Marker8 (SEQ ID NO:36) and marker locus SNP_Marker11 (SEQ ID NO:51), or within a genomic segment flanked by marker locus SNP_Marker1 (SEQ ID NO:1) and marker locus SNP_Marker2 (SEQ ID NO:6), which exhibit FORC resistance without a decrease in fruit quality or yield. In further embodiments, the present invention provides plants comprising introgressed DNA at marker locus SNP_Marker3 (SEQ ID NO:11), or at marker locus SNP_Marker9 (SEQ ID NO:41), or at marker locus SNP_Marker10 (SEQ ID NO:46) which exhibit FORC resistance without a decrease in fruit quality or yield.

Methods of producing plants comprising the reduced recombinant introgressions described herein are further provided. In some examples, donor DNA from a resistant donor parent is introgressed into a cultivated plant line (the recurrent parent line). In certain embodiments, SNP_Marker6 (SEQ ID NO:26), SNP_Marker8 (SEQ ID NO:36), and/or SNP_Marker11 (SEQ ID NO:51) are used to select the allele of the recurrent parent and SNP_Marker4 (SEQ ID NO:16), SNP_Marker5 (SEQ ID NO:21), SNP_Marker9 (SEQ ID NO:41), and/or SNP_Marker10 (SEQ ID NO:46) are used to select the allele of the resistance donor parent resulting in a reduced genomic interval lacking linkage drag associated traits associated with larger FORC resistance introgressions.

In certain embodiments, the invention provides methods of producing or selecting a *Cucumis sativus* plant exhibiting resistance to FORC comprising: a) crossing a *Cucumis sativus* plant provided herein with itself or with a second *Cucumis sativus* plant of a different genotype to produce one or more progeny plants; and b) selecting a progeny plant comprising said first introgressed allele or said second introgressed allele. In some embodiments, methods of the invention comprise selecting a progeny plant by detecting at least one polymorphism at a locus selected from the group consisting of marker locus SNP_Marker1 (SEQ ID NO:1), marker locus SNP_Marker2 (SEQ ID NO:6), marker locus SNP_Marker3 (SEQ ID NO:11), marker locus SNP_Marker4 (SEQ ID NO:16), marker locus SNP_Marker5 (SEQ ID NO:21), marker locus SNP_Marker6 (SEQ ID NO:26), marker locus SNP_Marker7 (SEQ ID NO:31), marker locus SNP_Marker8 (SEQ ID NO:36), marker locus SNP_Marker9 (SEQ ID NO:41), marker locus SNP_Marker10 (SEQ ID NO:46), and marker locus SNP_Marker11 (SEQ ID NO:51).

In further embodiments, progeny plants comprising reduced recombinant introgressions can be selected by detecting: a) a recurrent parent allele at marker locus SNP_Marker6 (SEQ ID NO:26), a recurrent parent allele at marker locus SNP_Marker8 (SEQ ID NO:36), a donor allele at marker locus SNP_Marker4 (SEQ ID NO:16), a donor allele at marker locus SNP_Marker5 (SEQ ID NO:21), a donor allele at marker locus SNP_Marker9 (SEQ ID NO:41), a donor allele at marker locus SNP_Marker10 (SEQ ID NO:46) on chromosome 6; b) a recurrent parent allele at marker locus SNP_Marker11 (SEQ ID NO:51), a donor allele at marker locus SNP_Marker4 (SEQ ID NO:16), a donor allele at marker locus SNP_Marker5 (SEQ ID NO:21), a donor allele at marker locus SNP_Marker9 (SEQ ID NO:41), a donor allele at marker locus SNP_Marker0 (SEQ ID NO:46) on chromosome 6; or c) a recurrent parent allele at marker locus SNP_Marker6 (SEQ ID NO:26), a recurrent parent allele at marker locus SNP_Marker8 (SEQ ID NO:36), a recurrent parent allele at marker locus SNP_Marker11 (SEQ ID NO:51), a donor allele at marker locus SNP_Marker4 (SEQ ID NO:16), a donor allele at marker locus SNP_Marker5 (SEQ ID NO:21), a donor allele at marker locus SNP_Marker9 (SEQ ID NO:41), a donor allele at marker locus SNP_Marker10 (SEQ ID NO:46) on chromosome 6.

Because genetically diverse plant lines can be difficult to cross, the introgression of FORC resistance alleles into cultivated lines using conventional breeding methods could require prohibitively large segregating populations for progeny screens with an uncertain outcome. Marker-assisted selection (MAS) is therefore essential for the effective introgression of FORC resistance alleles into elite cultivars. However, previously known markers for FORC resistance have failed to discriminate between donor DNA conferring disease resistance and donor DNA conferring deleterious traits. This has been further complicated by the previous inability to resolve the specific regions associated with disease resistance. For the first time, the present invention enables effective MAS by providing improved and validated markers for detecting genotypes associated with disease resistance without the need to grow large populations of plants to maturity in order to observe the phenotype.

I. Genomic Regions, Alleles, and Polymorphisms Associated With FORC Resistance in Cucumber Plants The invention provides novel introgressions of one or more alleles associated with disease resistance and fruit quality in cucumber plants, together with polymorphic nucleic acids and linked markers for tracking the introgressions during plant breeding.

Cucumber lines exhibiting FORC resistance are known in the art and may be used together with the novel trait-linked markers provided herein in accordance with certain embodiments of the invention. For example, PCT Patent Publication WO 2010/098670A1 describes resistance source URS189 and intermediate resistance source MC1278. PCT Patent Publication WO 2017/016908A1 describes another source of resistance to FORC. However, it was observed that introgressing FORC resistance from URS189 is associated with linkage drag, such as necrosis, poor fruit shape, agronomically unacceptable plant architecture.

Using the improved genetic markers and assays of the invention, Applicants were able to successfully identify novel FORC resistance regions associated with fewer deleterious traits when introgressed into a cultivated line. In certain embodiments, the invention provides cucumber plants comprising donor DNA from a FORC resistant line between marker locus SNP_Marker6 (SEQ ID NO:26) and marker locus SNP_Marker7 (SEQ ID NO: 31) on chromosome 6, or between marker locus SNP_Marker4 (SEQ ID NO:16) and marker locus SNP_Marker5 (SEQ ID NO:21) on chromosome 6, or between marker locus SNP_Marker6 (SEQ ID NO:26) and marker locus SNP_Marker11 (SEQ ID NO:51) on chromosome 6, or between marker locus SNP_Marker8 (SEQ ID NO:36) and marker locus SNP_Marker11 (SEQ ID NO:51) on chromosome 6, or between marker locus SNP_Marker1 (SEQ ID NO:1) and marker locus SNP_Marker2 (SEQ ID NO:6) on chromosome 3.

The novel introgressions provided herein confer robust resistance to FORC, while avoiding the reduction in fruit quality seen with conventional introgressions. In one embodiment of the invention, such a reduction in fruit quality is characterized by thinning and elongation of the neck of fruit of plants with an introgression conferring the poor fruit quality relative to plants lacking the introgression. This trait is highly undesirable because such a neck shape will make that part of the fruit rubberier due to increased rates of water loss. The invention therefore represents a significant advance by providing novel introgressions conferring robust resistance to FORC without poor fruit quality.

In other embodiments, the invention provides a plant comprising a recombinant introgression on chromosome 3 or 6 comprising a first allele conferring improved resistance to FORC relative to a plant lacking said first allele, wherein said plant does not exhibit reduced fruit quality compared to a plant lacking said first allele. In further embodiments, the plants comprising recombinant introgressions on both chromosomes 3 and 6 comprising alleles conferring improved resistance to FORC relative to a plant lacking said alleles, wherein said plant does not exhibit reduced fruit quality compared to a plant lacking said first allele. The recombinant introgression or introgressions may be deployed heterozygously or homozygously.

In another embodiment, the invention provides novel markers that may be used to identify a locus described herein, such as the markers set forth in Table 3. Other embodiments of the invention provide markers SNP_Marker1 (SEQ ID NO:1), SNP_Marker2 (SEQ ID NO:6), SNP_Marker3 (SEQ ID NO:11), SNP_Marker4 (SEQ ID NO:16), SNP_Marker5 (SEQ ID NO:21), SNP_Marker6 (SEQ ID NO:26), SNP_Marker7 (SEQ ID NO:31), SNP_Marker8 (SEQ ID NO:36), SNP_Marker9 (SEQ ID NO:41), SNP_Marker10 (SEQ ID NO:46), and SNP_Marker11 (SEQ ID NO:51), which have been shown to be genetically linked to FORC resistance in plants.

II. Introgression of Genomic Regions Associated with Disease Resistance

Marker-assisted introgression involves the transfer of a chromosomal region defined by one or more markers from a first genetic background to a second. Offspring of a cross that contain the introgressed genomic region can be identified by the combination of markers characteristic of the desired introgressed genomic region from a first genetic background and both linked and unlinked markers characteristic of the second genetic background.

The present invention provides novel accurate markers for identifying and tracking introgression of one or more of the genomic regions disclosed herein from a FORC resistant plant into a cultivated line. The invention further provides markers for identifying and tracking the novel introgressions disclosed herein during plant breeding, including the markers set forth in Table 3. Other embodiments of the invention provide markers SNP_Marker1 (SEQ ID NO:1), SNP_Marker2 (SEQ ID NO:6), SNP_Marker3 (SEQ ID NO:11), SNP_Marker4 (SEQ ID NO:16), SNP_Marker5 (SEQ ID NO:21), SNP_Marker6 (SEQ ID NO:26), SNP_Marker7 (SEQ ID NO:31), SNP_Marker8 (SEQ ID NO:36), SNP_Marker9 (SEQ ID NO:41), SNP_Marker1 (SEQ ID NO:46), and SNP_Marker11 (SEQ ID NO:51), which have been shown to be genetically linked to FORC resistance in plants.

Markers within or linked to any of the genomic intervals of the present invention may be useful in a variety of breeding efforts that include introgression of genomic regions associated with disease resistance into a desired genetic background. For example, a marker within 40 cM, 20 cM, 15 cM, 10 cM, 5 cM, 2 cM, or 1 cM of a marker associated with disease resistance described herein can be used for marker-assisted introgression of genomic regions associated with a disease resistant phenotype.

Cucumber plants comprising one or more introgressed regions associated with a desired phenotype wherein at least 10%, 25%, 50%, 75%, 90%, or 99% of the remaining genomic sequences carry markers characteristic of the recurrent parent germplasm are also provided. Cucumber plants comprising an introgressed region comprising regions closely linked to or adjacent to the genomic regions and markers provided herein and associated with a disease resistance phenotype are also provided.

III. Development of Disease Resistant Cucumber Varieties

For most breeding objectives, commercial breeders work within germplasm that is "cultivated," "cultivated type," or "elite." These cultivated lines may be used as recurrent parents or as a source of recurrent parent alleles during breeding. Cultivated or elite germplasm is easier to breed because it generally performs well when evaluated for horticultural performance. Many cultivated cucumber types have been developed and are known in the art as being agronomically elite and appropriate for commercial cultivation. However, the performance advantage a cultivated germplasm provides can be offset by a lack of allelic diversity. Breeders generally accept this tradeoff because progress is faster when working with cultivated material than when breeding with genetically diverse sources.

In contrast, when cultivated germplasm is crossed with non-cultivated germplasm, a breeder can gain access to novel alleles from the non-cultivated type. Non-cultivated germplasm may be used as a source of donor alleles during breeding. However, this approach generally presents significant difficulties due to fertility problems associated with crosses between diverse lines, and negative linkage drag from the non-cultivated parent. For example, non-cultivated cucumber types can provide alleles associated with disease resistance. However, these non-cultivated types may have poor horticultural qualities such as poor fruit shape, agronomically unacceptable plant architecture, and/or necrosis.

The process of introgressing desirable resistance genes from non-cultivated lines into elite cultivated lines while avoiding problems with linkage drag or low heritability is a long and often arduous process. In deploying alleles derived from wild relatives it is often desirable to introduce a minimal or truncated introgression that provides the desired trait but lacks detrimental effects. To aid introgression reliable marker assays are preferable to phenotypic screens. Success is furthered by simplifying genetics for key attributes to allow focus on genetic gain for quantitative traits such as disease resistance. Moreover, the process of introgressing genomic regions from non-cultivated lines can be greatly facilitated by the availability of accurate markers for MAS.

One of skill in the art would therefore understand that the alleles, polymorphisms, and markers provided by the invention allow the tracking and introduction of any of the genomic regions identified herein into any genetic background. In addition, the genomic regions associated with disease resistance disclosed herein can be introgressed from one genotype to another and tracked using MAS. Thus, the inventors' discovery of accurate markers associated with disease resistance will facilitate the development of cucumber plants having beneficial phenotypes. For example, seed can be genotyped using the markers of the present invention to select for plants comprising desired genomic regions associated with disease resistance. Moreover, MAS allows identification of plants homozygous or heterozygous for a desired introgression.

Inter-species crosses can also result in suppressed recombination and plants with low fertility or fecundity. For example, suppressed recombination has been observed for the tomato nematode resistance gene Mi, the Mla and Mlg genes in barley, the Yr17 and Lr20 genes in wheat, the Run1 gene in grapevine, and the Rma gene in peanut. Meiotic recombination is essential for classical breeding because it enables the transfer of favorable alleles across genetic backgrounds, the removal of deleterious genomic fragments, and pyramiding traits that are genetically tightly linked. Therefore, in the absence of accurate markers, suppressed recombination forces breeders to enlarge segregating populations for progeny screens in order to arrive at the desired genetic combination.

Phenotypic evaluation of large populations is time-consuming, resource-intensive and not reproducible in every environment. Marker-assisted selection offers a feasible alternative. Molecular assays designed to detect unique polymorphisms, such as SNPs, are versatile. However, they may fail to discriminate alleles within and among cucumber species in a single assay. Structural rearrangements of chromosomes such as deletions impair hybridization and extension of synthetically labeled oligonucleotides. In the case of duplication events, multiple copies are amplified in a single reaction without distinction. The development and validation of accurate and highly predictive markers are therefore essential for successful MAS breeding programs.

IV. Molecular Assisted Breeding Techniques

Genetic markers that can be used in the practice of the present invention include, but are not limited to, restriction fragment length polymorphisms (RFLPs), amplified fragment length polymorphisms (AFLPs), simple sequence repeats (SSRs), simple sequence length polymorphisms (SSLPs), single nucleotide polymorphisms (SNPs), insertion/deletion polymorphisms (Indels), variable number tandem repeats (VNTRs), and random amplified polymorphic DNA (RAPD), isozymes, and other markers known to those skilled in the art. Marker discovery and development in crop plants provides the initial framework for applications to marker-assisted breeding activities (U.S. Patent Pub. Nos.: 2005/0204780, 2005/0216545, 2005/0218305, and 2006/00504538). The resulting "genetic map" is the representation of the relative position of characterized loci (polymorphic nucleic acid markers or any other locus for which alleles can be identified) to each other.

Polymorphisms comprising as little as a single nucleotide change can be assayed in a number of ways. For example, detection can be made by electrophoretic techniques including a single strand conformational polymorphism (Orita, et al. (1989) *Genomics,* 8(2), 271-278), denaturing gradient gel electrophoresis (Myers (1985) *EPO* 0273085), or cleavage fragment length polymorphisms (Life Technologies, Inc., Gathersberg, MD), but the widespread availability of DNA sequencing often makes it easier to simply sequence amplified products directly. Once the polymorphic sequence difference is known, rapid assays can be designed for progeny testing, typically involving some version of PCR amplification of specific alleles (PASA; Sommer, et al. (1992) *Biotechniques* 12(1), 82-87), or PCR amplification of multiple specific alleles (PAMSA; Dutton and Sommer (1991) *Biotechniques,* 11(6), 700-7002).

Polymorphic markers serve as useful tools for assaying plants for determining the degree of identity of lines or varieties (U.S. Pat. No. 6,207,367). These markers form the basis for determining associations with phenotypes and can be used to drive genetic gain. In certain embodiments of methods of the invention, polymorphic nucleic acids can be used to detect in a cucumber plant a genotype associated with disease resistance, identify a cucumber plant with a genotype associated with disease resistance, and to select a cucumber plant with a genotype associated with disease resistance. In certain embodiments of methods of the invention, polymorphic nucleic acids can be used to produce a cucumber plant that comprises in its genome an introgressed locus associated with disease resistance. In certain embodiments of the invention, polymorphic nucleic acids can be used to breed progeny cucumber plants comprising a locus or loci associated with disease resistance.

Genetic markers may include "dominant" or "codominant" markers. "Codominant" markers reveal the presence of two or more alleles (two per diploid individual). "Dominant" markers reveal the presence of only a single allele. Markers are preferably inherited in codominant fashion so that the presence of both alleles at a diploid locus, or multiple alleles in triploid or tetraploid loci, are readily detectable, and they are free of environmental variation, i.e., their heritability is 1. A marker genotype typically comprises two marker alleles at each locus in a diploid organism. The marker allelic composition of each locus can be either homozygous or heterozygous. Homozygosity is a condition where both alleles at a locus are characterized by the same nucleotide sequence. Heterozygosity refers to different conditions of the allele at a locus.

Nucleic acid-based analyses for determining the presence or absence of the genetic polymorphism (i.e. for genotyping) can be used in breeding programs for identification, selection, introgression, and the like. A wide variety of genetic markers for the analysis of genetic polymorphisms are available and known to those of skill in the art. The analysis may be used to select for genes, portions of genes, QTL, alleles, or genomic regions that comprise or are linked to a genetic marker that is linked to or associated with disease resistance in cucumber plants.

As used herein, nucleic acid analysis methods include, but are not limited to, PCR-based detection methods (for example, TaqMan assays), microarray methods, mass spectrometry-based methods and/or nucleic acid sequencing methods, including whole genome sequencing. In certain embodiments, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

One method of achieving such amplification employs the polymerase chain reaction (PCR) (Mullis et al. (1986) Cold Spring Harbor Symp. Quant. Biol. 51:263-273; European Patent 50,424; European Patent 84,796; European Patent 258,017; European Patent 237,362; European Patent 201, 184; U.S. Pat. Nos. 4,683,202; 4,582,788; and 4,683,194), using primer pairs that are capable of hybridizing to the proximal sequences that define a polymorphism in its double-stranded form. Methods for typing DNA based on mass spectrometry can also be used. Such methods are disclosed in U.S. Pat. Nos. 6,613,509 and 6,503,710, and references found therein.

Polymorphisms in DNA sequences can be detected or typed by a variety of effective methods well known in the art including, but not limited to, those disclosed in U.S. Pat. Nos. 5,468,613, 5,217,863; 5,210,015; 5,876,930; 6,030, 787; 6,004,744; 6,013,431; 5,595,890; 5,762,876; 5,945, 283; 5,468,613; 6,090,558; 5,800,944; 5,616,464; 7,312, 039; 7,238,476; 7,297,485; 7,282,355; 7,270,981 and 7,250, 252 all of which are incorporated herein by reference in their entirety. However, the compositions and methods of the present invention can be used in conjunction with any polymorphism typing method to type polymorphisms in genomic DNA samples. These genomic DNA samples used include but are not limited to, genomic DNA isolated directly from a plant, cloned genomic DNA, or amplified genomic DNA.

For instance, polymorphisms in DNA sequences can be detected by hybridization to allele-specific oligonucleotide (ASO) probes as disclosed in U.S. Pat. Nos. 5,468,613 and 5,217,863. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labeled sequence-specific oligonucleotide probe.

Target nucleic acid sequence can also be detected by probe ligation methods, for example as disclosed in U.S. Pat. No. 5,800,944 where sequence of interest is amplified and hybridized to probes followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization (Borevitz et al., *Genome Res.* 13:513-523 (2003); Cui et al., *Bioinformatics* 21:3852-3858 (2005). On any one microarray, it is expected there will be a plurality of target sequences, which may represent genes and/or noncoding regions wherein each target sequence is represented by a series of overlapping oligonucleotides, rather than by a single probe. This platform provides for high throughput screening of a plurality of polymorphisms. Typing of target sequences by microarray-based methods is described in U.S. Pat. Nos. 6,799,122; 6,913,879; and 6,996, 476.

Other methods for detecting SNPs and Indels include single base extension (SBE) methods. Examples of SBE methods include, but are not limited, to those disclosed in U.S. Pat. Nos. 6,004,744; 6,013,431; 5,595,890; 5,762,876; and 5,945,283.

In another method for detecting polymorphisms, SNPs and Indels can be detected by methods disclosed in U.S. Pat. Nos. 5,210,015; 5,876,930; and 6,030,787 in which an oligonucleotide probe having a 5' fluorescent reporter dye and a 3' quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR, forward and reverse primers hybridize to a specific sequence of the target DNA flanking a polymorphism while the hybridization probe hybridizes to polymorphism-containing sequence within the amplified PCR product. In the subsequent PCR cycle DNA polymerase with 5' 3' exonuclease activity cleaves the probe and separates the reporter dye from the quencher dye resulting in increased fluorescence of the reporter.

In another embodiment, a locus or loci of interest can be directly sequenced using nucleic acid sequencing technologies. Methods for nucleic acid sequencing are known in the art and include technologies provided by 454 Life Sciences (Branford, CT), Agencourt Bioscience (Beverly, MA), Applied Biosystems (Foster City, CA), LI-COR Biosciences (Lincoln, NE, NimbleGen Systems (Madison, WI), Illumina (San Diego, CA), and VisiGen Biotechnologies (Houston, TX). Such nucleic acid sequencing technologies comprise formats such as parallel bead arrays, sequencing by ligation, capillary electrophoresis, electronic microchips, "biochips," microarrays, parallel microchips, and single-molecule arrays.

V. Definitions

The following definitions are provided to better define the present invention and to guide those of ordinary skill in the art in the practice of the present invention. Unless otherwise noted, terms are to be understood according to conventional usage by those of ordinary skill in the relevant art.

As used herein, the term "plant" includes plant cells, plant protoplasts, plant cells of tissue culture from which cucumber plants can be regenerated, plant calli, plant clumps and plant cells that are intact in plants or parts of plants such as pollen, flowers, seeds, leaves, stems, and the like.

As used herein, the term "population" means a genetically heterogeneous collection of plants that share a common parental derivation.

As used herein, the terms "variety" and "cultivar" mean a group of similar plants that by their genetic pedigrees and performance can be identified from other varieties within the same species.

As used herein, an "allele" refers to one of two or more alternative forms of a genomic sequence at a given locus on a chromosome.

A "quantitative trait locus" (QTL) is a chromosomal location that encodes for at least a first allele that affects the expressivity of a phenotype.

As used herein, a "marker" means a detectable characteristic that can be used to discriminate between organisms. Examples of such characteristics include, but are not limited to, genetic markers, biochemical markers, metabolites, morphological characteristics, and agronomic characteristics.

As used herein, the term "phenotype" means the detectable characteristics of a cell or organism that can be influenced by gene expression.

As used herein, the term "genotype" means the specific allelic makeup of a plant.

As used herein, "elite" or "cultivated" variety means any variety that has resulted from breeding and selection for superior agronomic performance. An "elite plant" refers to a plant belonging to an elite variety. Numerous elite varieties are available and known to those of skill in the art of cucumber breeding. An "elite population" is an assortment of elite individuals or varieties that can be used to represent the state of the art in terms of agronomically superior genotypes of a given crop species, such as cucumber. Similarly, an "elite germplasm" or elite strain of germplasm is an agronomically superior germplasm.

As used herein, the term "introgressed," when used in reference to a genetic locus, refers to a genetic locus that has been introduced into a new genetic background, such as through backcrossing. Introgression of a genetic locus can be achieved through plant breeding methods and/or by molecular genetic methods. Such molecular genetic methods include, but are not limited to, various plant transformation techniques and/or methods that provide for homologous recombination, non-homologous recombination, site-specific recombination, and/or genomic modifications that provide for locus substitution or locus conversion.

As used herein, the terms "recombinant" or "recombined" in the context of a chromosomal segment refer to recombinant DNA sequences comprising one or more genetic loci in a configuration in which they are not found in nature, for example as a result of a recombination event between homologous chromosomes during meiosis.

As used herein, the term "linked," when used in the context of nucleic acid markers and/or genomic regions, means that the markers and/or genomic regions are located on the same linkage group or chromosome such that they tend to segregate together at meiosis.

As used herein, "tolerance locus" means a locus associated with tolerance or resistance to disease. For instance, a tolerance locus according to the present invention may, in one embodiment, control tolerance or susceptibility to FORC.

As used herein, "tolerance" or "improved tolerance" in a plant refers to the ability of the plant to perform well, for example by maintaining yield, under disease conditions. Tolerance may also refer to the ability of a plant to maintain a plant vigor phenotype under disease conditions. Tolerance is a relative term, indicating that a "tolerant" plant is more able to maintain performance compared to a different (less tolerant) plant (e.g. a different plant variety) grown in similar disease conditions. One of skill will appreciate that plant tolerance to disease conditions varies widely, and can represent a spectrum of more-tolerant or less-tolerant phenotypes. However, by simple observation, one of skill can generally determine the relative tolerance of different plants, plant varieties, or plant families under disease conditions, and furthermore, will also recognize the phenotypic gradations of "tolerance."

As used herein "resistance" or "improved resistance" in a plant to disease conditions is an indication that the plant is more able to reduce disease burden than a non-resistant or less resistant plant. Resistance is a relative term, indicating that a "resistant" plant is more able to reduce disease burden compared to a different (less resistant) plant (e.g., a different plant variety) grown in similar disease conditions. One of skill will appreciate that plant resistance to disease conditions varies widely, and can represent a spectrum of more-resistant or less-resistant phenotypes. However, by simple observation, one of skill can generally determine the relative resistance of different plants, plant varieties, or plant families under disease conditions, and furthermore, will also recognize the phenotypic gradations of "resistant."

As used herein, "resistance allele" means the nucleic acid sequence associated with tolerance or resistance to disease.

The term "about" is used to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." When used in conjunction with the word "comprising" or other open language in the claims, the words "a" and "an" denote "one or more," unless specifically noted. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

EXAMPLES

Example 1. Phenotyping FORC Resistance

Several methods exist for assaying FORC resistance in cucumber plants, including seedling assays, adult plant assays, and field trials.

Seedling Assays

Seedlings can be assayed by preparing liquid inoculum by growing FORC in 0.5 L of Czapek Dox broth media in a shaker at 30 rpm and 25° C. for 5-7 days, or until there are enough sporangia to make up a sporangia suspension of 4-5×$10^5$ sporangia/mL. Czapek Dox broth media is commercially available, or can be made by mixing 30 g sucrose, 2 g $NaNO_3$, 1 g $K_2HPO_4$, 0.5 g $MgSO_4$, 0.5 g KCl, and 0.01 g $FeSO_4$ in 1 L deionized water setting the pH at 7.3 at room temperature. Media should be sterilized at 121° C. for 15 minutes. A concentration of 4×$10^5$ sporangia/mL may be used to evaluate intermediate resistance, while a concentration of 5×$10^5$ sporangia/mL may be used to evaluate full resistance. Plants are inoculated at the time of seedling transplant, which is when the cotyledons are fully expanded (generally 4-7 days after sowing). To inoculate, the seedlings are carefully removed from the germination pots and the roots of the seedling are placed in a glass vessel with a small amount of the prepared suspension for three minutes. Seedlings are removed only by touching the cotyledons without touching the stems and transplanted into the experimental trays with soil. Proper coverage of the roots should be ensured to avoid drying out, and the soil should be evenly humid throughout the tray. Throughout the inoculation process, the inoculum used for dipping should be refreshed regularly from the inoculum stock, at least once per tray. Inoculated seedlings should be kept at a 20° C. After 4-5 days post inoculation (dpi) sensitive controls are evaluated for signs of wilting. If wilting is absent in the susceptible controls, the temperature may be reduced to 18° C. during the night. Repeat this check at 8 dpi. Direct sunlight should be avoided. Evaluation may be done at 9, 13, and 16 dpi. Seedlings are scored on a scale of 1-9 where 1 corresponds to plants with no symptoms; 3 corresponds to plants that are still green but smaller compared to other plants and developing new secondary roots despite dead points; 5 corresponds to plants where the cotyledons/1st leaf are still green but are overall very small with no growth after inoculation and brown roots with absent or minor secondary root development; 7 corresponds to seedlings that are dead 16 dpi; 8 corresponds to seedlings that are dead 13 dpi; and 9 corresponds to seedlings dead at 9 dpi. In an accurate assay, 90% of the susceptible controls should be dead and 90% of the resistant controls (e.g. URS189) should be scored a 1.

Adult Plant Assays

While seedling assays can be used to screen germplasm quickly for resistance and rough mapping of resistance QTLs, adult plant assays may be used to further confirm the results. Adult plants may be assayed by preparing inoculation material as for the seedling assay described above, but adjusting the inoculum to a concentration to 1×$10^6$ spores/ml. Plants are sown in peat-blocks (for example 7 cm×7 cm blocks or 10 cm×10 cm blocks). Seedlings are maintained in the nursery (for example at 19-25° C. with 16 h/day artificial light cycles) until the appearance of the first leaf, which is approximately 14-18 days after sowing. The plants are transplanted in their peat-block to peat bags with no more than five plants per bag and grown in the greenhouse (for example at 19-25° C. during the day and 10-14° C. during the night). Several nights with temperatures as low as 10° C. should be included for optimal infection. Experiments during the summer months should be avoided because prolonged exposure to warmer nights (>16° C.) will inhibit infection. During the trial, the greenhouse should be kept free of other pests, plants should be trained on a wire but not pruned, and fruits should be removed as they develop. Plants should be inoculated with FORC during the development of the second leaf, which is approximately 1-3 days post-transplant. To inoculate the plants, 20 ml of prepared FORC suspension is introduced on two sides of the peat-block (i.e. 40 ml of inoculum per plant). The plants in the trial are evaluated when all susceptible controls show symptoms of FORC infection (approximately 45-60 days post inoculation). The scoring is done on a 1-9 scale where 1 corresponds to full resistance, which is recognized by the absence of wilting and only small amount of burn in older leaves; 3 corresponds to plants where wilting is absent, but where older leaves are burnt for the first meter of the ground; 5 corresponds to plants with some wilting of green leaves; 7 is scored if most green leaves are wilting; and a 9 is scored for plants where all leaves have wilted. In certain examples, 6 replicates with 3 plants per variety are included, or 5 replicates with 2 plants per variety. As the positive (resistant) control one can use, e.g. URS189. Any variety can be a positive control if 100% of the positive control plants score below a 5 at the time of scoring. The negative control should be any susceptible variety, e.g. Corona, if it fits within the validation norm at the end of the experiment (i.e. 100% of susceptible control plants should score above a 3 and at least 80% should score above a 5). One can include an intermediate resistant variety, e.g. MC1278, which might be especially useful when trying to work on a scale of resistance, rather than determining high resistance or susceptibility.

Example 2. QTL Mapping of FORC Resistance

Fully resistant donor URS189 was crossed with two different highly susceptible inbred lines (TELE and BAK). From these crosses, two F2:3 populations segregating for FORC resistance were created and used for QTL mapping. FORC resistance was determined using the seedling root dip assay described above. Each population was genotyped with >500 markers across the whole cucumber genome. The data was analyzed using the "scanone" function in the R statistical package. Following the analysis, three QTLs were identified, which were located on chromosomes 2, 3, and 6 (Table 1). These three QTLs were found in both populations. Further analysis where different stacks of QTLs were tested showed that the QTL on chromosome 3 and chromosome 6 were most closely associated with resistance to FORC.

TABLE 1

Mapping of FORC resistance from URS189

| Population | Chromosom | Position | 1-LOD Interval (cM) | Maxmium LOD ADPC | Maxmium LOD MDI | $R^2$ |
|---|---|---|---|---|---|---|
| BAK/URS139 | 2 | 29 | 24.0-39.0 | 5.33 | 5.12 | 23.50% |
| BAK/URS189 | 3 | 42.2 | 39.9-50.2 | 6.93 | 6.35 | 32.40% |
| BAK/URS189 | 6 | 13 | 0-32.0 | 4.06 | 4.09 | 7.50% |
| TELE/URS189 | 2 | 34.4 | 17.4-47.4 | 4.46 | 4.09 | 13.80% |
| TELE/URS189 | 3 | 46.2 | 44.2-60.9 | 7.35 | 7.29 | 26.20% |
| TELE/URS189 | 6 | 13 | 9.0-22.0 | 4.95 | 4.9 | 14.90% |

Example 3. Identification of Deleterious Traits Associated with FORC Resistance The newly identified QTLs from chromosome 3 and chromosome 6 were introgressed into elite breeding material. There it was observed that the locus on chromosome 6 came with extensive linkage drag (Table 2). Problems with yield, plant architecture, fruit quality, and necrosis were observed. In terms of fruit quality, the shape of the neck was especially undesirable (FIG. 1). A thinner and elongated neck was observed in the fruit of plants with the chromosome 6 introgression, which is highly undesirable because such a neck shape will make that part of the fruit rubberier due to increased rates of water loss. Consumers perceive these fruits as spoiled. Furthermore, plants with the chromosome 6 introgression were observed to have increased flower numbers per node. The optimal number is one flower per node as this provides the best balance between plant vigor and fruit size. Increased numbers of flowers per node will have a negative effect on fruit size and plant vigor. This can be compensated by removal of the flowers, but that constitutes an undesired extra labor expense for growers. The 3 lines shown in table 2 were genetically analyzed and it was found that the introgression on chromosome 6 was larger in line 1, which has the worst linkage drag. The inventors therefore hypothesized that reduction of the introgression size may result in a phenotype without linkage drag. The locus on chromosome 6 was therefore fine mapped to remove the linkage drag associated with the resistance locus.

TABLE 2

Quantification of agronomic trait changes compared to the recurrent parent for lines with the introgression on chromosome 6. Specific drag is observed for flowers per node, number of side shoots, and shape of the neck of the fruit. The disease score is on a scale 1-9 (1 = resistant, 9 = susceptible). Scoring scales are indicated with the trait. Letters behind the scores indicated the grouping in post-hoc analysis of the data.

| | | | Yield | | | | Fruit traits | | | | Plant architecture traits | | | | | | | |
|---|---|---|---|---|---|---|---|---|---|---|---|---|---|---|---|---|---|---|
| | | Resistance Disease | KG per plant | | Fruits per plant | | Spines (1-5) | | Neck (1-4) | | Necrosis (1-9) | | Flowers per node | | Leaf size (CM) | | Side shoots (1-4) | |
| QTL | Pedigree | score | LSM | Level | LSM | Level | LSM | Level | LSM | Level | LSM | Level | LSM | Level | LSM | Leve | LSM | Level |
| RP | Recurrent Parent | 8.3 | 9.49 | A | 72.58 | A | 4.04 | A | 2.21 | CD | 4.31 | E | 1.18 | E | 31.32 | A | 1.48 | C |
| Chr6 | Line 1 | 1.7 | 6.55 | C | 54.95 | C | 1.81 | C | 3.63 | AB | 5.40 | C | 1.47 | BCD | 28.52 | CD | 0.50 | D |
| | Line 2 | 3 | 8.53 | AB | 70.40 | AB | 1.56 | C | 3.00 | AB | 4.45 | DE | 1.88 | A | 28.60 | C | 2.30 | AB |
| | Line 3 | 5.2 | 8.55 | AB | 73.55 | A | 1.69 | C | 2.88 | BC | 5.08 | C | 1.73 | AB | 29.14 | C | 2.40 | AB |

Example 4. Fine Mapping of FORC Resistance QTLs

Both FORC resistance loci were further fine-mapped. From the populations used for the original mapping, BC1F8 populations were developed using only BC1F7 parents that were homozygous for the QTL region on chromosome 3 or 6. In total, there were 27 families with the BAK background and 41 families with the TELE background. These populations were phenotyped using the seedling plant assay described. Twelve additional markers were developed between 17.2 and 43.8 cM for the chromosome 6 region and nine additional markers were developed between 38.4 and 56 cM for the chromosome 3 region. These new markers were used to genotype the BC1F8 populations. The data were analyzed with the statistical programming language "R" using the 1me4 package. Families with the same haplotype were combined into one haplotype group. For each haplotype group, the phenotypic score was determined using a mixed effects model. These phenotypic scores were subsequently used in a pairwise comparison to find a reduced QTL interval. Using this approach the interval for the chromosome 3 region was reduced to a 14.9 cM interval between SNP_Marker1 (SEQ ID NO:1) and SNP_Marker2. In addition, it was found that SNP_Marker3 (SEQ ID NO:11) is tightly linked to the FORC resistance found on chromosome 3. The region on chromosome 6 was reduced to a 13 cM interval between SNP_Marker6 (SEQ ID NO:26) and SNP_Marker7. Further analysis indicated that the absence of the 0.4 cM interval between SNP_Marker4 (SEQ ID NO:16) and SNP_Marker5 (SEQ ID NO:21) from donor URS189 provides susceptible phenotype, demonstrating that reduction of the URS189 introgression to this small interval is sufficient to generate a FORC resistant phenotype in cucumber without linkage drag. The inventors developed additional markers, SNP_Marker8 (SEQ ID NO:36), SNP_Marker9 (SEQ ID NO:41), SNP_Marker10 (SEQ ID NO:46), and SNP_Marker11 (SEQ ID NO:51) to accurately select linkage drag free elite cucumber plants that can be used as FORC resistance donors in a cucumber breeding program (Table 3).

TABLE 3

Markers used in the fine mapping of FORC resistance QTLs.

| Marker name | Chromosome | Physical position CCL genome | SNP position | CCL->trait | Full Sequence (SEQ ID NO.) | Fwd Primer (SEQ ID NO.) | Rev primer (SEQ ID NO.) | Probe 1 (SEQ ID NO.) | Probe 2 (SEQ ID NO.) | SNP position in Full Sequence |
|---|---|---|---|---|---|---|---|---|---|---|
| SNP_Marker1 | 3 | 13564345-13562602 | 13563433 | A->G | 1 | 2 | 3 | 4 | 5 | 911 |
| SNP_Marker2 | 3 | 22338928-22336780 | 22338746 | C->T | 6 | 7 | 8 | 9 | 10 | 177 |
| SNP_Marker3 | 3 | 17602681-17602881 | 17602782 | G->C | 11 | 12 | 13 | 14 | 15 | 102 |
| SNP_Marker4 | 6 | 5809437-5809637 | 5809537 | G->C | 16 | 17 | 18 | 19 | 20 | 101 |
| SNP_Marker5 | 6 | 5875574-5874685 | 5875197 | T->G | 21 | 22 | 23 | 24 | 25 | 378 |
| SNP_Marker6 | 6 | 4904952-4902777 | 4904085 | C->T | 26 | 27 | 28 | 29 | 30 | 868 |
| SNP_Marker7 | 6 | 8038097-8039661 | 8038585 | A->G | 31 | 32 | 33 | 34 | 35 | 489 |
| SNP_Marker8 | 6 | 4904957-4905214 | 4905024 | T->C | 36 | 37 | 38 | 39 | 40 | 67 |
| SNP_Marker9 | 6 | 5869011-5868830 | 5868909 | C->T | 41 | 42 | 43 | 44 | 45 | 102 |
| SNP_Marker10 | 6 | 5900505-5900877 | 5900726 | A->T | 46 | 47 | 48 | 49 | 50 | 221 |
| SNP_Marker11 | 6 | 7044929-7042669 | 7040820 | G->A | 51 | 52 | 53 | 54 | 55 | 1849 |

The invention claimed is:

1. A *Cucumis sativus* plant of a cultivated variety comprising a recombinant chromosomal segment on chromosome 6, wherein said chromosomal segment comprises a *Fusarium oxysporum* f.sp. *radicis cucumerinum* (FORC) resistance allele that confers an increased resistance to FORC to said plant when compared to a plant not comprising said allele, wherein said chromosomal segment lacks a deleterious allele genetically linked to said FORC resistance allele that confers necrosis or decreased fruit quality to said plant when present, wherein said chromosomal segment comprising said resistance allele is found in cucumber line URS189, and wherein said chromosomal segment is flanked by marker locus SNP_Marker4 having SEQ ID NO: 16 and marker locus SNP_Marker5 having SEQ ID NO:21.

2. The *Cucumis sativus* plant of claim 1, wherein said plant further comprises a second recombinant chromosomal segment on chromosome 3 that comprises a FORC resistance allele, wherein said second chromosomal segment comprising said resistance allele is found in cucumber line URS189, and wherein said second chromosomal segment is flanked by marker locus SNP_Marker1 having SEQ ID NO:1 and marker locus SNP_Marker2 having SEQ ID NO: 6.

3. A plant part of the *Cucumis sativus* plant of claim 1, wherein said plant part comprises said recombinant chromosomal segment.

4. A method for producing a *Cucumis sativus* plant exhibiting resistance to FORC, comprising:

a) crossing the *Cucumis sativus* plant of claim 1 with itself or with a second *Cucumis sativus* plant of a different genotype to produce one or more progeny plants; and b) selecting a progeny plant comprising said recombinant chromosomal segment, whereby said progeny plant exhibits resistance to FORC.

5. The method of claim 4, wherein selecting said progeny plant comprises detecting the presence of at least one allele comprising a marker locus selected from the group consisting of marker locus SNP_Marker4 having SEQ ID NO:16, marker locus SNP_Marker5 having SEQ ID NO:21, and marker locus SNP_Marker9 having SEQ ID NO:41.

6. The method of claim 4, wherein said progeny plant is an $F_2$-$F_6$ progeny plant.

7. The method of claim 4, wherein producing said progeny plant further comprises backcrossing.

* * * * *

SEQUENCE LISTING

```
<160> NUMBER OF SEQ ID NOS: 55

<210> SEQ ID NO 1
<211> LENGTH: 1741
<212> TYPE: DNA
<213> ORGANISM: Cucumis sativus

<400> SEQUENCE: 1

ttaatgcagc ttgtgcaatc ttcttgtatt ttttgtttcc tcttctgtct taatggttct     60

tatgcttcag actcgaagaa ttttttttct ttaacctttt gactgatacc actcataaaa    120

attgtttttt attcagaact ttgtagttga gcttttacga aagccttggt aattcctttt    180

tttttaact tgttcaaggt agatttctca ttatggcaac aatcacatgt gttgctcaat    240

tccaagttct tttgccccaa attgtatatc ttcgaatttc tctgtttttt tttttgaact    300

ttcagtcttg agaatcctag atttcctttg tttttttattt ttaacttttc tcattcagga    360

aaggtttctt cattacagca acaatcactt ctattgctgg atttctaagt gcttttgccc    420

caaactatac atctctgtta atccttcgct gtctagttgg tgttgggttg ggaggtggcc    480

ctgtacttgc atcctggttc ttggaattca ttcctgctcc tgaaagaggc acttggatgg    540

ttattttttc agcattctgg accattggaa caatccttga agcttctttg gcatgggtat    600

aatctagctt tctgttgtag ttcagtgcac gttcttgcta cattttcttt tctcttatta    660

aatcaataat taaaaataag aagaagaaaa gataagattc caataggaag ttatgttcat    720

tgcctgactc attttgagtt gatcaacttt gacactgcta gcaaatgaga tctatttttg    780

gagatttttt tacacttcta aattcatgta gcatttctaa tattccattc cctttgataa    840

tatttcatag tagctatatg gagactgttt gtggtgtagt ctaaccggtt agttcattgg    900

ttgtcagttt rctgttgttc taacaggtca gaattaaata ttagcttaac aactttgtta    960

gttatgctgt tatctgttaa tccatttgta caaggagctt tctcgtctaa ttgtagctat   1020

taacgataac aagttcttcg agcagttaaa attcataatc tgatgaaaaa aagtggtatg   1080

gtatataata gtgtggttga aaatttaatt tatgtcctgt tgtcatgact cattagtggt   1140

tgatgtcata ggtatctaaa ggtgaaacaa aattaacttt ctttaaattg ttgcacatgg   1200

aggtactcag actgttcact tgaattttta accttatttt tttactctgc ttttttagga   1260

caattttttt tcttgttggt tcttccattc attttttttac tctatgcttt ccagctgcac   1320

cattgaaaag ggttgcaatc acctttatgt tttatgccct tgtatttaca gattgtcatg   1380
```

-continued ccaaaattag gatggagatg gctactcgca ttttcttctt taccttcatt tctcctacta 1440
ctcttctatc aatctactcc agagtcccca cggtatctct gtttacaagg tagaacaagt 1500
gatgcagcta ttattttaga gaaaatagca catcgtaata gaacaaatct ccccccctgga 1560 attcttgttt ctagtcactc gtatgatttt gaggagcaag gtactgctgt ggaagatgtg 1620
catttgctct caccaacaca aactaaagtt gaaacttctc aagcaacaac ctctagtatg 1680
gttgctttct caccattgtt gaagcttctt tctcgagaac tgcttttgtc cacattgctg 1740
c 1741

<210> SEQ ID NO 2
<211> LENGTH: 25
<212> TYPE: DNA
<213> ORGANISM: Artificial sequence
<220> FEATURE:
<223> OTHER INFORMATION: primer

<400> SEQUENCE: 2
tggtgtagtc taaccggtta gttca 25

<210> SEQ ID NO 3
<211> LENGTH: 28
<212> TYPE: DNA
<213> ORGANISM: Artificial sequence
<220> FEATURE:
<223> OTHER INFORMATION: primer

<400> SEQUENCE: 3
aacagcataa ctaacaaagt tgttaagc 28

<210> SEQ ID NO 4
<211> LENGTH: 21
<212> TYPE: DNA
<213> ORGANISM: Artificial sequence
<220> FEATURE:
<223> OTHER INFORMATION: probe

<400> SEQUENCE: 4
tgttagaaca acagtaaact g 21

<210> SEQ ID NO 5
<211> LENGTH: 18
<212> TYPE: DNA
<213> ORGANISM: Artificial sequence
<220> FEATURE:
<223> OTHER INFORMATION: probe

<400> SEQUENCE: 5
tagaacaaca gcaaactg 18

<210> SEQ ID NO 6
<211> LENGTH: 2149
<212> TYPE: DNA
<213> ORGANISM: Cucumis sativus

<400> SEQUENCE: 6
gtggcagatt tagaatacac agacagtgaa acacccaaca aacagttggc gacaccttcc 60
aattgatcac attcacgatc caagttttga agagctctat gagcaatact cgttccctct 120
tcagcgaggt cacagttctc tccacaaatc ttcgacgcca tcaataaagc tggaagygat 180
ttaggatcct catgactacc caacactttt ctcaacagat tcaaagcagt caagttttca 240

-continued

```
cctgcaccat aataacaaag agctaaagca tgatgcagtt cttgtcgatg tagaatccca    300
ggaggcaatt cctctatttg acctgctaaa gcccttgtat cccctgatat tattaaagca    360
aaagagagat gatccaagat tgatggatcc caatcaatcc ttttaagaac aacttttcta    420
agtagtatca taaataaaag tatagcttct tcaatattgt ttttcggaac aaacgagctg    480
tccatttgag accggagatt cggagggcaa gcttcacttc cactgtacag aagaaaaatg    540
gcaaactctt tctgaattcg agcagtggtt tccgcatcaa ggttccactg atgaagaagt    600
gcccgccggt atgaaaggat cgcttcttga gaagcatcag ctagcttcca taactcgggt    660
agcagctcca cggcttttgt aactgtctcc tgcaatttac aatcagcacc aaagttttca    720
ggcaagcctt cgggaaatga agattcaagt atgtccagaa taactttgca agattgagca    780
gcttctgcaa gaataatgaa aaatgaagat cagctacaca taaatgtttt taatctaaga    840
aaccactcaa gcacctcctt ttccctgact ctttttacg  gagtgaattc caagattttg    900
caaggttttt atatagggaa gtagcctttt gcgggcaatc ccaaaaatgg aaaatcacaa    960
tgaattctca tattccaacc aagactcaac accagagttg taaggcattt cataaaaaaa   1020
aactcatatt aaagaggtag acaaaagaga tagattccca aaactaagaa acggtacctc   1080
cgaacctccc aaggccttcc aatgattttg ctttgagaag gatggcttcc aagagtaaac   1140
tgacagcatg catagacatt ggcggggcag taaaattttg tgatcgtttc cgtagacgat   1200
ctcctctcct agatatggag atcattattt tactggttat agcagtgata tcaattcctt   1260
caaatacatg aagagcagct tcaatatttc ctttttgata ttcatatctt cccagcaatg   1320
ctcttgcttc cttcaaacaa taggcataaa ttaattgcaa cccttttccc tccaaactaa   1380
acaaagctag atgttctaga aaacatcggt atatgattcc tcgaacctaa taatcacctc   1440
gatccaaatc accccaattt tcctttttcc taactctgtt ctatttcaaa agcagcaatt   1500
tttgcgatac atatcagaca gacaaaataa agaagattga cagaagaaag agtagttaac   1560
ttatgagttg tttcatttca atttatcttc acgattctca tataaagtac tataaatttt   1620
tctcgctaaa cttcattctt gtaaaaacaa taccttcagg gtgataatca ttgacaactg   1680
accaaaaact catacaggta gagatcaatc tgaactcaat attaatgaaa agacaacttg   1740
atcagaaaga aagcttgctt atgtcactct actatcttgc ttcttctgga ttgtgacaat   1800
caatcatcag aaataagttt gtaaatgaga caatagacca agaaagatgc ctttcaacct   1860
agaaagctta agaattctaa cctcataatt caaacaacca ctctcgcgaa gcgaagactc   1920
agcttcttct atattcccaa tttctggttt gttgatgatc tcgccagtcc gtgaagagtg   1980
tccacttcct gagttctcga aagccgaagg tgatttcaat gctggaatca tattatctcc   2040
agctttttc  tcaccagaac ataaacactt cattatcttc cttatattct cccctttcc    2100
agtgctcctc cccctcttaa tcttaacgtc actcttcata ttgttcgac              2149
```

<210> SEQ ID NO 7
<211> LENGTH: 24
<212> TYPE: DNA
<213> ORGANISM: Artificial sequence
<220> FEATURE:
<223> OTHER INFORMATION: primer

<400> SEQUENCE: 7

```
cacaaatctt cgacgccatc aata                                            24
```

<210> SEQ ID NO 8
<211> LENGTH: 25

<212> TYPE: DNA
<213> ORGANISM: Artificial sequence
<220> FEATURE:
<223> OTHER INFORMATION: primer

<400> SEQUENCE: 8
tgttgagaaa agtgttgggt agtca 25

<210> SEQ ID NO 9
<211> LENGTH: 18
<212> TYPE: DNA
<213> ORGANISM: Artificial sequence
<220> FEATURE:
<223> OTHER INFORMATION: probe

<400> SEQUENCE: 9
aagctggaag tgatttag 18

<210> SEQ ID NO 10
<211> LENGTH: 15
<212> TYPE: DNA
<213> ORGANISM: Artificial sequence
<220> FEATURE:
<223> OTHER INFORMATION: probe

<400> SEQUENCE: 10
ctggaagcga tttag 15

<210> SEQ ID NO 11
<211> LENGTH: 201
<212> TYPE: DNA
<213> ORGANISM: Cucumis sativus

<400> SEQUENCE: 11
aaagtttaaa tatatggagg gcaaaccaaa acaagaacca actctaaatt tagagatgaa 60
agtagtgcta ataagaaagc caattgaatg tgtgagtacc cstagaagta gtttgtgtat 120
atatatataa attgtgaagt ctaccagttg acccaatcac acatcctaat ccacttatta 180
tttgttttct tttgggatca t 201

<210> SEQ ID NO 12
<211> LENGTH: 31
<212> TYPE: DNA
<213> ORGANISM: Artificial sequence
<220> FEATURE:
<223> OTHER INFORMATION: primer

<400> SEQUENCE: 12
gaaagtagtg ctaataagaa agccaattga a 31

<210> SEQ ID NO 13
<211> LENGTH: 25
<212> TYPE: DNA
<213> ORGANISM: Artificial sequence
<220> FEATURE:
<223> OTHER INFORMATION: primer

<400> SEQUENCE: 13
gggtcaactg gtagacttca caatt 25

<210> SEQ ID NO 14
<211> LENGTH: 20
<212> TYPE: DNA
<213> ORGANISM: Artificial sequence
<220> FEATURE:

-continued

<223> OTHER INFORMATION: probe

<400> SEQUENCE: 14
tgtgtgagta cccctagaag 20

<210> SEQ ID NO 15
<211> LENGTH: 18
<212> TYPE: DNA
<213> ORGANISM: Artificial sequence
<220> FEATURE:
<223> OTHER INFORMATION: probe

<400> SEQUENCE: 15
tgtgagtacc cgtagaag 18

<210> SEQ ID NO 16
<211> LENGTH: 201
<212> TYPE: DNA
<213> ORGANISM: Cucumis sativus

<400> SEQUENCE: 16
tcgaaggctc tactcagctg gcgtaataaa tcaaccaggt tgtgactcaa aatctgatgt 60
tttccaacac taaagaatcc cttcctgcaa gattccacgc scgcaacctt cccattgcaa 120
agcttggcct tacaaattca aagaaagaaa aacggccaaa ttcatcagta cagtataaat 180
ctaaaaaagt atagccatag t 201

<210> SEQ ID NO 17
<211> LENGTH: 25
<212> TYPE: DNA
<213> ORGANISM: Artificial sequence
<220> FEATURE:
<223> OTHER INFORMATION: primer

<400> SEQUENCE: 17
cactaaagaa tcccttcctg caaga 25

<210> SEQ ID NO 18
<211> LENGTH: 21
<212> TYPE: DNA
<213> ORGANISM: Artificial sequence
<220> FEATURE:
<223> OTHER INFORMATION: primer

<400> SEQUENCE: 18
taaggccaag ctttgcaatg g 21

<210> SEQ ID NO 19
<211> LENGTH: 13
<212> TYPE: DNA
<213> ORGANISM: Artificial sequence
<220> FEATURE:
<223> OTHER INFORMATION: probe

<400> SEQUENCE: 19
cacgcccgca acc 13

<210> SEQ ID NO 20
<211> LENGTH: 12
<212> TYPE: DNA
<213> ORGANISM: Artificial sequence
<220> FEATURE:
<223> OTHER INFORMATION: probe

<400> SEQUENCE: 20
acgcgcgcaa cc 12

<210> SEQ ID NO 21
<211> LENGTH: 890
<212> TYPE: DNA
<213> ORGANISM: Cucumis sativus

<400> SEQUENCE: 21
gagtatgtct aatgatcggt ggttctgact ctacaacttt tattttgtta gttctgacga 60
agtcgctgct tgcaagaggc ttatagagaa ggttggactt aagggattcc aggtaattgt 120
ttgatgagag atcaaagtta ggtcttgaag tgaccttgtg ttgcaattgg cagactattt 180
gtcactgttc acaagctcaa tactttgcgt ttgtcttttg aaagagatat gttattgagc 240
tccaactttt gttttcaatg gtttttccca tatatttttt ctaaatctgg tatttcccac 300
attttttttt tgatatcgac tcaattcttt agtttcagct atggaatcat ttaaattttc 360
tttactgaag tttcctckag cagttataaa cttccctttc cttcaatttt taaactatgt 420
ctaggacgat tgatttttat ataagtttta tgtgttctta actacttgta tacaaagtat 480
aaactatagc gtgttatgtt acaaatgtaa catattctgg cagattggta agacaaaggt 540
gtttcttaga gctggtcaga tggccgagct tgatgcgctc agaactgaga tcttaggacg 600
atcagcaagt attattcagc ggaaggttcg ttcttatctg gcgcgtagaa gttttgtatt 660
gcttcggagg tcggctatac gtttgcagtc tgcttgtaga ggtaataaat tgtcatcaac 720
taactgttgt actggtagac ctgctttcat aagaagtcct ttgtaattag ctaagaatta 780
ctgagttttg atccatgttg gtttcaggac aactttctcg agaagtattt aagggtttga 840
ggagagaagc ttcttcttta atgattcaaa ggaatttgcg catgcatctc 890

<210> SEQ ID NO 22
<211> LENGTH: 29
<212> TYPE: DNA
<213> ORGANISM: Artificial sequence
<220> FEATURE:
<223> OTHER INFORMATION: primer

<400> SEQUENCE: 22
gactcaattc tttagtttca gctatggaa 29

<210> SEQ ID NO 23
<211> LENGTH: 27
<212> TYPE: DNA
<213> ORGANISM: Artificial sequence
<220> FEATURE:
<223> OTHER INFORMATION: primer

<400> SEQUENCE: 23
aaaaatcaat cgtcctagac atagttt 27

<210> SEQ ID NO 24
<211> LENGTH: 17
<212> TYPE: DNA
<213> ORGANISM: Artificial sequence
<220> FEATURE:
<223> OTHER INFORMATION: probe

<400> SEQUENCE: 24
aactgctaga ggaaact 17

<210> SEQ ID NO 25

-continued

<211> LENGTH: 14
<212> TYPE: DNA
<213> ORGANISM: Artificial sequence
<220> FEATURE:
<223> OTHER INFORMATION: probe

<400> SEQUENCE: 25
tgctcgagga aact 14

<210> SEQ ID NO 26
<211> LENGTH: 2176
<212> TYPE: DNA
<213> ORGANISM: Cucumis sativus

<400> SEQUENCE: 26
gctgcttgca acatttccat cggtaatata acgagcacct gatagaagag atcccaaccc 60
aatcctgcat gaaaacgatc atagttaaac aattaactca ccgaattctt acaagttcaa 120
aataacagtg tttaaaggaa atatacagac ccgggaaaca gatacatgtt atttgcttga 180
tttacatggc caaactttcc attacctgca agttatttta cagaaagtca tattaaacta 240
taagatacag ggctagatcc gaaacttaaa aagctcgtgc aatcccatag gaaaacttta 300
aattgatcgt ttaggtatga tgctatttca cacattttat ttttcagaac ataaaagata 360
ccaagtgcaa cgttctcaaa agggcttcca ctagcgaaca caatgttttc tccagcgtac 420
ttgaaagcat cagcagcagt gcattcagct ggtaaaagaa aaaaaggata accagttgta 480
actgcaaata gctagctaat ttgaaaattt ttgcatcctt ataaacaaac agaccgttca 540
tggtgggatt tgacattgca aatattgcag gtttacttga atcagattcc cgcattgcct 600
tgagaaccta gagtaatccc atcaaatatg agaactagaa gaggaaagtg tacccaaaaa 660
ttgacactct cctacatgga ctttgccatt aactaaatgg ataaaggaca atgaggtctc 720
aagttcatta catctgtcct gtaattatga ggctaaacga acaaaagaca atgatgcatg 780
taatttactc gagaggtgtt caatttcctt tctcctatcc tccattattg cttttatctg 840
aggaaacgtc taaaataatc tccactcyag agaaaaagat gaatgagagg tggatttctt 900
aagttgctta ttttacaaat ttataacaag aaagtgtgag ataaagcatg gacgactaaa 960
aaacaagtgg cataaatgaa aataacggaa acatcataca tattgatgtt gttgagataa 1020
tactttttgg aaattgaagt aagccccaac taacgaaaaa aagagaggat atgtacctcc 1080
tcattgaaga taccgccaac tcctgacaga ccaagaagaa catggggcct aaccctttc 1140 acctgaacag tgattaaaat ttcatccata aatcttaatg gggatggtca aaaactactg 1200
aagagtaatg gcagaatcct ctctgagtgt tgaggaaatt agctatgtat ccctaaccat 1260
gaagggagtt tgagaaagct taccacttct aataaattgg ctccttcact gagtccctcg 1320
agctctcttg gatctttagc aaatggtgca gctgctggat caatgtttgt tctttctttt 1380
gtgataaggc cctgtacaaa gaaataattt attttgctct gatgacatat gtaacatgga 1440
gttaaaaatc tagcagcata accttgctaa aatcatcgca tcacaatcat gataataagg 1500
tgtgaagagc atataacaat taaatacact tcatagagat taaaaaacca acaatagatc 1560
tgaaaagtta agatcaatgt caatttcata agaaatcaat attctataaa tataacactt 1620
gcacaatagt tgaccttttt gggatcagat gtaagaaaac aaatatgatg tagataaaaa 1680
ttgagaacaa ggaaggagga gcattcttca cagaaaaaaa ttaaaatcaa agtcaagaag 1740
tagtacaaga aagagcttta cccaaaagat acggtagtag gaaaggcaag acaacaataa 1800
tgacaaacaa ttcatttccc gttcaatcaa acattaaaca aaaagtttta cacatcttta 1860

-continued aaatatgctt tatcatgttc atgaatgata atttttacgt gctagaaatt tgagtagttc 1920
aaacgtaaac aaaacaagct taatgttaag cttccccagc aggttgatca tgataattaa 1980
aatcaactca atgacttcat gaaattaata aatagaagtg ttaaagtaac atagacatga 2040
atatataagc tagagcagag acatgactat acctgacaac cattacatag tgctaaaaga 2100
aatgacaatt ttctttttca tttaatatgt aatttgtaat ctacaaagac aattggtcaa 2160
atagatgagg ttaatc 2176

<210> SEQ ID NO 27
<211> LENGTH: 29
<212> TYPE: DNA
<213> ORGANISM: Artificial sequence
<220> FEATURE:
<223> OTHER INFORMATION: primer

<400> SEQUENCE: 27
tccattattg cttttatctg aggaaacgt 29

<210> SEQ ID NO 28
<211> LENGTH: 28
<212> TYPE: DNA
<213> ORGANISM: Artificial sequence
<220> FEATURE:
<223> OTHER INFORMATION: primer

<400> SEQUENCE: 28
gcaacttaag aaatccacct ctcattca 28

<210> SEQ ID NO 29
<211> LENGTH: 19
<212> TYPE: DNA
<213> ORGANISM: Artificial sequence
<220> FEATURE:
<223> OTHER INFORMATION: probe

<400> SEQUENCE: 29
aatctccact ctagagaaa 19

<210> SEQ ID NO 30
<211> LENGTH: 15
<212> TYPE: DNA
<213> ORGANISM: Artificial sequence
<220> FEATURE:
<223> OTHER INFORMATION: probe

<400> SEQUENCE: 30
tccactccag agaaa 15

<210> SEQ ID NO 31
<211> LENGTH: 1572
<212> TYPE: DNA
<213> ORGANISM: Cucumis sativus

<400> SEQUENCE: 31
gatctatatt caaggaggat tttcagaaag ttccaggagg aattggtaga aactcttgcc 60
aatcctgcaa ccaaaattga tgacacagga accattgcta cctatcgagt agcaaaattt 120
ggggaagacc ataaagccca tgctgttagt tttaattcat tagagatgaa agctaattgc 180
agttgtcaac tgtttgaata ttcaggaata atttgcaggc atatattagc agtttttagg 240
gcaaaaaatg ttcttacact tccttctcaa tatgtattga aacggtggac cagaaatgcc 300

-continued

```
agaaatggag ctgtaacaga tgatcataat tcagaactac caaatgaagc tggagattct    360
tctactgtca ggtacaataa tcttcgtcaa gaagcaatca agtatgttga agaaggagcg    420
aagtcaattc atatttataa tgtggctgtg gatgccctaa aagaggcctc tagaaaggtt    480
tctgctgtra agaatcgggg ccctggagct actaacggtg atgttatggc caatggagtt    540
gttgggcctt tggttgcaac agaagagaat cagacaccaa cctatcaatc agtggttagt    600
ctcaatagtt tgcagtttta tttaaatcct acgaatttca gtgttttatt catgatcctc    660
accccacctc ctgagacaag tgatttagac ttatttaccc caaaaaatga gcattgtgtt    720
tgagagatgt ctaaatcatt agggcagcat actatatttc atgagtctct tgatgacgaa    780
ctgttgtagg gttcagtggt aaggtttact ttttaacgag atgaacctgg agagttggaa    840
gattcgttag ttaatgataa taataagctt agatttgggt tgaatagata ttactgtgtc    900
atacttgtcc tatatgtgta ctttggttgc attgtattca ttaccttttc ccatcctgct    960
gatgtgttca tccacaaatc tccagatggg tacagattgg ttcttacgat caaaatcaat   1020
tttttttttg cctcctgtgt actttattgt atattttggt gaggcaccaa cttttcaata   1080
attgaaccta attatttatg gactaaactt ttcttcaatg catctgtttg tgctgtttct   1140
tagtgcattt ttataaagat gaattaacca gaagactgct cttactgtct ttttacatct   1200
acttttctct tcgagattgt aaaggggaaa agttagatat agagtgtgtt tggtttaact   1260
tttcaagtac ttaattttga aaataagtca ttttggaaaa aattgaaaca cttggcaacc   1320
acccaatgta gcttttttaa aactatcaaa gtttattaca gtttttatca aaggagttca   1380
aataagaata acttgataaa aagtaatttt ttccctagtc aatccaaata ggccaatagc   1440
caaaaaaaaa aaggaatacc aagaagataa tggaggttga cattttctta tttgttctct   1500
gttctctgtt gtgttgtttc cttttccagg aacaaaagga gaagaaaatt cgtgagcttt   1560
ctgcactata gt                                                        1572
```

```
<210> SEQ ID NO 32
<211> LENGTH: 25
<212> TYPE: DNA
<213> ORGANISM: Artificial sequence
<220> FEATURE:
<223> OTHER INFORMATION: primer

<400> SEQUENCE: 32

cctaaaagag gcctctagaa aggtt                                            25


<210> SEQ ID NO 33
<211> LENGTH: 24
<212> TYPE: DNA
<213> ORGANISM: Artificial sequence
<220> FEATURE:
<223> OTHER INFORMATION: primer

<400> SEQUENCE: 33

gccataacat caccgttagt agct                                             24


<210> SEQ ID NO 34
<211> LENGTH: 16
<212> TYPE: DNA
<213> ORGANISM: Artificial sequence
<220> FEATURE:
<223> OTHER INFORMATION: probe

<400> SEQUENCE: 34

tctgctgtaa agaatc                                                      16
```

<210> SEQ ID NO 35
<211> LENGTH: 14
<212> TYPE: DNA
<213> ORGANISM: Artificial sequence
<220> FEATURE:
<223> OTHER INFORMATION: probe

<400> SEQUENCE: 35
tgctgtgaag aatc 14

<210> SEQ ID NO 36
<211> LENGTH: 258
<212> TYPE: DNA
<213> ORGANISM: Cucumis sativus

<400> SEQUENCE: 36
gaatggtatg aatctttatg tggaagtaca atatcatctc ttcttttagt tttaaatttg 60
gaagacygaa gatgttaaaa atgcctagtt tgccgcggaa accttagggt atattaagag 120
gatttgtctt atggtttttg gtgaaaccac ttgcagactg cttatggaaa aaattataag 180
cggggttgta tctctttcca tacaaacatc caatagttgt ttcttaatga aagcagtctt 240
tctaaatttg attaggca 258

<210> SEQ ID NO 37
<211> LENGTH: 35
<212> TYPE: DNA
<213> ORGANISM: Artificial sequence
<220> FEATURE:
<223> OTHER INFORMATION: primer

<400> SEQUENCE: 37
gaatctttat gtggaagtac aatatcatct cttct 35

<210> SEQ ID NO 38
<211> LENGTH: 20
<212> TYPE: DNA
<213> ORGANISM: Artificial sequence
<220> FEATURE:
<223> OTHER INFORMATION: primer

<400> SEQUENCE: 38
cgcggcaaac taggcatttt 20

<210> SEQ ID NO 39
<211> LENGTH: 17
<212> TYPE: DNA
<213> ORGANISM: Artificial sequence
<220> FEATURE:
<223> OTHER INFORMATION: probe

<400> SEQUENCE: 39
aacatcttca gtcttcc 17

<210> SEQ ID NO 40
<211> LENGTH: 15
<212> TYPE: DNA
<213> ORGANISM: Artificial sequence
<220> FEATURE:
<223> OTHER INFORMATION: probe

<400> SEQUENCE: 40
catcttcggt cttcc 15

<210> SEQ ID NO 41
<211> LENGTH: 182
<212> TYPE: DNA
<213> ORGANISM: Cucumis sativus

<400> SEQUENCE: 41
ttgtggtagt ttttcaacta tagtgccatg tttcacaatc ttacttacta acatgaacca 60
ctttcagcat cccattctcg gtcgaagacc tatcgaactc aytgcaagag aaagatttct 120
cgggcgtgaa gccagccgac gaactacttg agaacccagc cttccaattt ttacacgagt 180
aa 182

<210> SEQ ID NO 42
<211> LENGTH: 22
<212> TYPE: DNA
<213> ORGANISM: Artificial sequence
<220> FEATURE:
<223> OTHER INFORMATION: primer

<400> SEQUENCE: 42
catcccattc tcggtcgaag ac 22

<210> SEQ ID NO 43
<211> LENGTH: 20
<212> TYPE: DNA
<213> ORGANISM: Artificial sequence
<220> FEATURE:
<223> OTHER INFORMATION: primer

<400> SEQUENCE: 43
gcttcacgcc cgagaaatct 20

<210> SEQ ID NO 44
<211> LENGTH: 17
<212> TYPE: DNA
<213> ORGANISM: Artificial sequence
<220> FEATURE:
<223> OTHER INFORMATION: probe

<400> SEQUENCE: 44
tctcttgcag tgagttc 17

<210> SEQ ID NO 45
<211> LENGTH: 18
<212> TYPE: DNA
<213> ORGANISM: Artificial sequence
<220> FEATURE:
<223> OTHER INFORMATION: probe

<400> SEQUENCE: 45
ttctcttgca atgagttc 18

<210> SEQ ID NO 46
<211> LENGTH: 373
<212> TYPE: DNA
<213> ORGANISM: Cucumis sativus

<400> SEQUENCE: 46
gaacattact agaacaattt tggaaacata acatatccat aaactttacg tcttcacaaa 60
acaccaaata ataatttcaa ctacaaaaca attcgagaaa cagtcctcta accaggtaca 120
acaaaactaa actcaagcta atcttcgtag aaaatatata aataaataaa gtctgttaca 180
gttacaacca cccaattcaa gggaaaccac atcaatgtta waaacttcta gaaagttctt 240
taaaaaaaat aaatataaga aacaagccaa atggtcagtc tttctcaaga atcctattca 300
acatcatgaa ggtcgtggaa cttatcattg cctgaaaaac tgtgggtgat cactaccaac 360
acgtgtactg agc 373

<210> SEQ ID NO 47
<211> LENGTH: 22
<212> TYPE: DNA
<213> ORGANISM: Artificial sequence
<220> FEATURE:
<223> OTHER INFORMATION: primer

<400> SEQUENCE: 47
ccacccaatt caagggaaac ca 22

<210> SEQ ID NO 48
<211> LENGTH: 33
<212> TYPE: DNA
<213> ORGANISM: Artificial sequence
<220> FEATURE:
<223> OTHER INFORMATION: primer

<400> SEQUENCE: 48
gactgaccat ttggcttgtt tcttatattt att 33

<210> SEQ ID NO 49
<211> LENGTH: 19
<212> TYPE: DNA
<213> ORGANISM: Artificial sequence
<220> FEATURE:
<223> OTHER INFORMATION: probe

<400> SEQUENCE: 49
catcaatgtt aaaaacttc 19

<210> SEQ ID NO 50
<211> LENGTH: 19
<212> TYPE: DNA
<213> ORGANISM: Artificial sequence
<220> FEATURE:
<223> OTHER INFORMATION: probe

<400> SEQUENCE: 50
catcaatgtt ataaacttc 19

<210> SEQ ID NO 51
<211> LENGTH: 2262
<212> TYPE: DNA
<213> ORGANISM: Cucumis sativus
<220> FEATURE:
<221> NAME/KEY: misc_feature
<222> LOCATION: (2246)..(2248)
<223> OTHER INFORMATION: n is a, c, g, or t
<220> FEATURE:
<221> NAME/KEY: misc_feature
<222> LOCATION: (2254)..(2254)
<223> OTHER INFORMATION: n is a, c, g, or t
<220> FEATURE:
<221> NAME/KEY: misc_feature
<222> LOCATION: (2256)..(2256)
<223> OTHER INFORMATION: n is a, c, g, or t

<400> SEQUENCE: 51
gttcaggcgc tcagtaagtt tttgttttta tgtcctttct tctttagagg ccattggagg 60
gtatacaaat gggttgaatt tcgaatgata tccatacttt ttaaggttta ttatccgtct 120

-continued

```
ttactagggg tgtacataag ccgggttgga ggaaaattat ggaccaaccc gaagtatccg    180
gttggcaaaa aaaatgaacc ctactggttc attatgtaag ggtcaaacca acccaaccca    240
tattaaaaat ttaaaagaga aatggtcatt ttacttccat ggtagtttca atatattgta    300
ctaaaaaaga aaaccctgaa aaacagtaaa tagcccaact tcagtaactt atgtttttct    360
agctcatctc gtagtaccca atgcttcggt gtatttgatg tcgaattaca tgacataatt    420
cttggtgagt tggcagtaat ttagtggtgg ttctaggtct aaagaagaaa attagaaaat    480
tattctttaa atttataaga aattggcaaa attcagtttc ttcttttagg tagtttattt    540
ctcctaaatt tctgccaact cactatcatt ccaagttcat tttcagcaat cttaaatctt    600
cacaaaataa ttgaaaaatg ttaaaataca agggactaat tgaaaaatat actaaaagat    660
atatttagac cattatattg tacaaatttg aattatgaca tcaagagatt cttttccaag    720
ctctggacat cttgaacatc cttttttttt cctttgcagc tcacccatgg ttgcaggatg    780
atagtcgtcg tataccttta gatatattaa tctataagtt ggtcaaatca tacctgcaag    840
ctactccttt caaacgtgca gctatgaagg ttaaagattc ttctttttgt ttcttatttg    900
gttgctggta ttagaaatta ttccgtccct tcaaaaacac ctatgcaatc atatcttatt    960
ttcttaattg agcttcgatg ttttcattgt caaacctaaa ttgtttttca atcctctgat   1020
cgtaaaagct tccatttcag gctctctcaa aagctttgtc agaaactgaa ctcttttatc   1080
ttagagctca gtttgcattg ttggaaccaa atcacgatgg gcgtgttggg cttgataact   1140
tcaaaatggt cagtacttct cttcaccctg atttcttttt ttttatagag caggactaat   1200
acaatcatca ctctccttca ctgtgtgttt tgactcataa atacctatgc tctaggcttt   1260
aatgcggaac gcaacggatg ctatgaggga gtcaagggtt catgaaattg taaattcggt   1320
agggttcttt taactcaatt cttatcttca tgctagattg taaatatagt tattacttga   1380
atttttttact atgctggttt cagatttcta tcttaattag gaactaggaa gtactgttgt   1440
tttgtttaaa tttttctttt tttacctccg ccaatgttta gacttgctta cacgcatctg   1500
gactaatctc ataggacaac ccatatcacc ttagaacatt tattttaaat tttatgttta   1560
ttctgtttag atctagaata tttatttaat ccttgtacat gcataaaaat tactagaatc   1620
gacttgggtc tttcaattat tctttttttat ccaaggccat tgattgattt taggcaaaaa   1680
taaaataaaa cttgtatgaa ggttcaaatg attgaataaa ggttaaattg taaatttggt   1740
tccaaagcag tacattagaa tgtagtaatt gtgattttaa aagttagaat ttagtcgatt   1800
tggtacataa ttaaatttag atatgaaaca attttgatca ctgaaatarg ataccatttt   1860
tcagttggag ccccttgcct acagaagaat ggactttgag gagttctgtg ctgcttcaat   1920
cagtacacat caattggaag ctcttgaccg gtgggagcag atagcctgtg tggcctttga   1980
gcatttcgag cgtgagggca accgggtgat atcagttgaa gaattagcta aggtttgttc   2040
attttctact ctttgaaaat tcacacataa atctaatcgg ttcttacaat attctgtttc   2100
gaaaatgcag gaattaaacc ttggttcctc agcacactct atccttaaag agtggattcg   2160
aggagatggg aagcttagtt ttcttgggta tacaaagttt ttacatggtg tcaccctacg   2220
tagctcaaat acaagacacc attagnnntt tttncntttt tt                       2262
```

<210> SEQ ID NO 52
<211> LENGTH: 39
<212> TYPE: DNA
<213> ORGANISM: Artificial sequence
<220> FEATURE:
<223> OTHER INFORMATION: primer -continued

```
<400> SEQUENCE: 52

atttagtcga tttggtacat aattaaattt agatatgaa                          39


<210> SEQ ID NO 53
<211> LENGTH: 26
<212> TYPE: DNA
<213> ORGANISM: Artificial sequence
<220> FEATURE:
<223> OTHER INFORMATION: primer

<400> SEQUENCE: 53

gaactcctca aagtccattc ttctgt                                        26


<210> SEQ ID NO 54
<211> LENGTH: 21
<212> TYPE: DNA
<213> ORGANISM: Artificial sequence
<220> FEATURE:
<223> OTHER INFORMATION: probe

<400> SEQUENCE: 54

tgatcactga aataagatac c                                             21


<210> SEQ ID NO 55
<211> LENGTH: 19
<212> TYPE: DNA
<213> ORGANISM: Artificial sequence
<220> FEATURE:
<223> OTHER INFORMATION: probe

<400> SEQUENCE: 55

atcactgaaa taggatacc                                                19
```